(12) United States Patent
Davey et al.

(10) Patent No.: US 11,453,912 B2
(45) Date of Patent: Sep. 27, 2022

(54) METHODS AND APPARATUSES FOR ESTIMATING PARAMETERS IN A PREDICTIVE MODEL FOR USE IN SEQUENCING-BY-SYNTHESIS

(71) Applicant: LIFE TECHNOLOGIES CORPORATION, Carlsbad, CA (US)

(72) Inventors: Melville Davey, Westbrook, CT (US); Michael Meyer, Ithaca, NY (US); Marcin Sikora, Burlingame, CA (US); Simon Cawley, Oakland, CA (US); Kirk Pastorian, Temecula, CA (US)

(73) Assignee: Life Technologies Corporation, Carlsbad, CA (US)

( * ) Notice: Subject to any disclaimer, the term of this patent is extended or adjusted under 35 U.S.C. 154(b) by 855 days.

(21) Appl. No.: 16/364,336

(22) Filed: Mar. 26, 2019

(65) Prior Publication Data

US 2019/0367980 A1    Dec. 5, 2019

Related U.S. Application Data

(63) Continuation of application No. 13/967,665, filed on Aug. 15, 2013, now Pat. No. 10,273,540, which is a continuation-in-part of application No. 13/283,320, filed on Oct. 27, 2011, now Pat. No. 8,666,678.

(60) Provisional application No. 61/775,322, filed on Mar. 8, 2013, provisional application No. 61/684,221, filed on Aug. 17, 2012, provisional application No. 61/407,377, filed on Oct. 27, 2010.

(51) Int. Cl.
*C12Q 1/6874* (2018.01)
*G16B 30/00* (2019.01)
*G16B 99/00* (2019.01)

(52) U.S. Cl.
CPC .......... *C12Q 1/6874* (2013.01); *G16B 30/00* (2019.02); *G16B 99/00* (2019.02)

(58) Field of Classification Search
None
See application file for complete search history.

(56) References Cited

U.S. PATENT DOCUMENTS

| | | | |
|---|---|---|---|
| 5,750,341 A | 5/1998 | Macevicz |
| 6,210,891 B1 | 4/2001 | Nyren et al. |
| 6,258,568 B1 | 7/2001 | Nyren |
| 6,274,320 B1 | 8/2001 | Rothberg et al. |
| 6,404,907 B1 | 6/2002 | Gilchrist et al. |
| 6,780,591 B2 | 8/2004 | Williams et al. |
| 6,828,100 B1 | 12/2004 | Ronaghi |
| 6,833,246 B2 | 12/2004 | Balasubramanian |
| 6,911,327 B2 | 6/2005 | Mcmillan et al. |
| 7,037,687 B2 | 5/2006 | Williams et al. |
| 7,133,782 B2 | 11/2006 | Odedra |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,323,305 B2 | 1/2008 | Leamon et al. |
| 7,335,762 B2 | 2/2008 | Rothberg et al. |
| 7,348,181 B2 | 3/2008 | Walt et al. |
| 7,424,371 B2 | 9/2008 | Kamentsky |
| 7,575,865 B2 | 8/2009 | Leamon et al. |
| 7,645,596 B2 | 1/2010 | Williams et al. |
| 7,782,237 B2 | 8/2010 | Ronaghi et al. |
| 7,785,862 B2 | 8/2010 | Kim et al. |
| 7,835,871 B2 | 11/2010 | Kain et al. |
| 7,875,440 B2 | 1/2011 | Williams et al. |
| 7,948,015 B2 | 5/2011 | Rothberg et al. |
| 8,666,678 B2 | 3/2014 | Davey et al. |
| 10,273,540 B2 * | 4/2019 | Davey ................... G16B 30/00 |
| 2002/0172948 A1 | 11/2002 | Perlin |
| 2003/0219797 A1 | 11/2003 | Zhao et al. |
| 2004/0018506 A1 | 1/2004 | Koehler et al. |
| 2004/0142330 A1 | 7/2004 | Nyren et al. |
| 2004/0197793 A1 | 10/2004 | Hassibi et al. |
| 2004/0197845 A1 | 10/2004 | Hassibi et al. |

(Continued)

FOREIGN PATENT DOCUMENTS

| GB | 2461127 A | 12/2009 |
|---|---|---|
| WO | WO-9957321 A1 | 11/1999 |

(Continued)

OTHER PUBLICATIONS

454 Sequencing System Software Manual Version 2.6 Part B : GS Run Processor, GS Reporter, GS Run Browser, GS Support Tool, available at http://genepool.bio.ed.ac.uk/Gene_Pool/454_software/Manuals/454SeqSys_SWManualv2.6 PartB May2011.pdf (last visited Aug. 31, 2012) (document dated May 2011 ).
Agah et al., "A multi-enzyme model for pyrosequencing," Nucleic Acids Res., 32(21):1-15 (2004).
Ahmadian et al., "Pyrosequencing: History, biochemistry and future," Clinica Chimica Acta, 363:83-94 (2006).

(Continued)

*Primary Examiner* — John S Brusca

(57) ABSTRACT

A method of estimating a parameter related to sequencing of a sample nucleic acid template includes: receiving signal data relating to nucleotide incorporation events resulting from a series of flows of nucleotides onto an array of wells including (i) a first well containing the sample nucleic acid template and (ii) a plurality of other sample-containing wells; determining sequence information for the sample nucleic acid template using signal data from the first well; and constructing a phase-state model for a set of nucleotide flows that contributed at least in part to the sequence information, wherein the model includes a signal correction parameter that is determined using signal data from the plurality of other sample-containing wells.

7 Claims, 8 Drawing Sheets

Specification includes a Sequence Listing.

(56) References Cited

U.S. PATENT DOCUMENTS

| | | |
|---|---|---|
| 2005/0084851 A1 | 4/2005 | Ronaghi et al. |
| 2006/0040297 A1 | 2/2006 | Leamon et al. |
| 2006/0147935 A1 | 7/2006 | Linnarsson |
| 2007/0092872 A1 | 4/2007 | Rothberg et al. |
| 2007/0219367 A1 | 9/2007 | Shchepinov et al. |
| 2007/0281300 A1 | 12/2007 | Russell et al. |
| 2008/0182757 A1 | 7/2008 | Heiner et al. |
| 2009/0024331 A1 | 1/2009 | Tomaney et al. |
| 2009/0026082 A1 | 1/2009 | Rothberg et al. |
| 2009/0053724 A1 | 2/2009 | Roth et al. |
| 2009/0105959 A1 | 4/2009 | Braverman et al. |
| 2009/0127589 A1 | 5/2009 | Rothberg et al. |
| 2009/0176200 A1 | 7/2009 | Wakita et al. |
| 2009/0312188 A1 | 12/2009 | Duer et al. |
| 2010/0035252 A1 | 2/2010 | Rothberg et al. |
| 2010/0035253 A1 | 2/2010 | Gordon et al. |
| 2010/0063743 A1 | 3/2010 | Gordon et al. |
| 2010/0088255 A1 | 4/2010 | Mann |
| 2010/0105052 A1 | 4/2010 | Drmanac et al. |
| 2010/0137143 A1 | 6/2010 | Rothberg et al. |
| 2010/0160172 A1 | 6/2010 | Erlich et al. |
| 2010/0173303 A1 | 7/2010 | Ronaghi et al. |
| 2010/0188073 A1 | 7/2010 | Rothberg et al. |
| 2010/0192032 A1 | 7/2010 | Chen et al. |
| 2010/0197507 A1 | 8/2010 | Rothberg et al. |
| 2010/0199155 A1 | 8/2010 | Kermani et al. |
| 2010/0209922 A1 | 8/2010 | Williams et al. |
| 2010/0267043 A1 | 10/2010 | Braverman et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2011/0213563 A1 | 9/2011 | Chen et al. |
| 2011/0230358 A1 | 9/2011 | Rava |
| 2011/0246084 A1 | 10/2011 | Ronaghi et al. |
| 2011/0257889 A1 | 10/2011 | Klammer et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0294115 A1 | 12/2011 | Williams et al. |
| 2012/0035062 A1 | 2/2012 | Schultz et al. |
| 2012/0037961 A1 | 2/2012 | Rothberg et al. |
| 2012/0040844 A1 | 2/2012 | Rothberg et al. |
| 2012/0172241 A1 | 7/2012 | Rearick et al. |
| 2012/0173158 A1 | 7/2012 | Hubbell |
| 2012/0173159 A1 | 7/2012 | Davey et al. |
| 2014/0051584 A1 | 2/2014 | Davey et al. |
| 2014/0222399 A1 | 8/2014 | Davey et al. |

FOREIGN PATENT DOCUMENTS

| | | |
|---|---|---|
| WO | WO-0220837 A2 | 3/2002 |
| WO | WO-03020895 A2 | 3/2003 |
| WO | WO-2005040425 A2 | 5/2005 |
| WO | WO-2007098049 A2 | 8/2007 |
| WO | WO-2008076406 A2 | 6/2008 |
| WO | WO-2008092150 A1 | 7/2008 |
| WO | WO-2008092155 A2 | 7/2008 |
| WO | WO-2007098049 A3 | 8/2008 |
| WO | WO-2009117119 A1 | 9/2009 |
| WO | WO-2009158006 A2 | 12/2009 |
| WO | WO-2010047804 A1 | 4/2010 |
| WO | WO-2010077859 A2 | 7/2010 |
| WO | WO-2010138182 A2 | 12/2010 |
| WO | WO-2011120964 A1 | 10/2011 |
| WO | WO-2011156707 A2 | 12/2011 |
| WO | WO-2012058459 A2 | 5/2012 |

OTHER PUBLICATIONS

Aksyonov et al., "Multiplexed DNA sequencing-by-synthesis," Anal. Biochem., 348:127-138 (2006).

Balzer et al., "Characteristics of 454 pyrosequencing data-enabling realistic simulation with flowsim," Bioinformatics, 26:i420-i425 (2010).

Brockman et al., "Quality scores and SNP detection in sequencing-by-synthesis systems," Genome Research, 18:763-770 (2008).

Chapter 2, "Machine-Learning Foundations: The Probabilistic Framework", In: Baldi, P. and Brunak, S., "Bioinformatics: The Machine Learning Approach, 2"d Edition, The MIT Press, 47-65 (2001).

Droege et al., "The Genome Sequencer FLX™ System-Longer reads, more applications, straight forward bioinformatics and more complete data sets," J. Biotechnol., 136:3-10 (2008).

El Toukhy, "An Integrated System for De Novo DNA Sequencing," Dissertation, Stanford University, Jun. 2006.

Eltoukhy, H., et al., "Modeling and Base-Calling for DNA Sequencing-By-Synthesis", 2006 IEEE International Conference on Acoustics, Speech, and Signal Processing, vol. 2, May 2006, II-1032-II-1035.

EP07750981.8, Extended European Search Report, dated Apr. 22, 2009.

EP11837111.1, Extended European Search Report dated Apr. 28, 2015, 4 pages.

Erlich et al. Alta-Cyclic: a self-optimizing base caller for next-generation sequencing Nature Methods vol. 5, pp. 679-682 and supplementary figures and methods (Year: 2008).

Extended European Search Report in EP16184914.6 dated Feb. 10, 2017, 6 pages.

Fakhrai-Rad et al., "Pyrosequencing™: An Accurate Detection Platform for Single Nucleotide Polymorphisms," Hum. Mutat., 19:479-485 (2002).

Finotello et al., "Comparative analysis of algorithms for whole-genome assembly of pyrosequencing data," Briefings in Bioinformatics Advance Access, 1-12 (Oct. 21, 2011 ).

Fuller et al., "The challenges of sequencing by synthesis", Nature Biotechnology, vol. 27, No. 11, Nov. 2009, 1013-1023.

Garcia et al., "Mutation detection by pyrosequencing: sequencing of exons 5-8 of the p53 tumor suppressor gene," Gene, 253(2):249-257 (2000) (see whole document, including Fig. 4).

Genome Sequencer FLX System Software Manual, version 2.3 Part B : GS Run Processor—GS Reporter—GS Run Browser—GS Support Tool, available at http://http://sequence.otago.ac.nz/download/ManuaiPartB.pdf (last visited Aug. 29, 2013) (document dated Oct. 2009).

Guarizadeh, B., "Method Development and Applications of Pyrosequencing Technology," Doctoral Dissertation, Royal Institute of Technology, Stockholm, Sweden (2003).

Huse et al., "Accuracy and quality of massively parallel DNA pyrosequencing," Genome Biology, 8(7):R143.1-R143.9 (2007).

International Preliminary Report on Patentability, International Appl. No. PCT/US2011/058134, dated Jul. 30, 2013.

Ji et al., "BM-BC: A Bayesian method of base calling for Solexa sequence data," Department of Biostatistics, The University of Texas M. D. Anderson Cancer Center, Houston, Texas, U.S.A. (http://odin.mdacc.tmc.edu/-ylii/BMBC/bmbc-ie2.pdf), 1-27, 2010.

Kao et al., "BayesCall: A model-based base-calling algorithm for high-throughput short-read sequencing," Genome Research, vol. 19, No. 10, Oct. 2009, 1884-1895.

Langaee et al., "Genetic variation analyses by Pyrosequencing," Mutation Research, 573: 96-102 (2005).

Leamon et al., "Cramming More Sequencing Reactions onto Microreactor Chips", Chemical Reviews, vol. 107, No. 8, Aug. 2007, pp. 3367-3376.

Ledergerber et al., "Base-calling for next-generation sequencing platforms," Briefings in Bioinformatics Advance Access, 12(5):489-497 (Jan. 18, 2011 ).

Lysholm et al., "FAAST: Flow-space Assisted Alignment Search Tool," BMC Bioinformatics 2011,12:293 (http://www.biomedcentral.com/1471-2105/12/293), pp. 1-7 (2011).

Margulies et al., "Genome Sequencing in Microfabricated High-Density Picolitre Reactors", Nature, vol. 437, No. 15, 2005, pp. 376-380.

Massingham et al., "All Your Base: a fast and accurate probabilistic approach to base calling," Euroclean Bioinformatics Institute, Wellcome Trust Genome Cam12us, Hinxton, Cambridgeshire, UK (http://www.ebi.ac.uk/goldman-srv/AYB/references/ayb_revised.pdf), Oct. 26, 2011, 1-26.

(56) References Cited

OTHER PUBLICATIONS

Metzker, "Emerging technologies in DNA sequencing," Genome Research, 15:1767-1776 (2005).
Metzker, "Sequencing technologies—The next generation," Nature Reviews Genetics, vol. 11, No. 1, Jan. 2010, pp. 31-46.
PCT/EP2011/054817, International Search Report dated Jun. 16, 2011.
PCT/US2007/04187, International Search Report, dated Jun. 16, 2008.
PCT/US2011/058134, International Search Report and Written Opinion, dated Feb. 15, 2012.
Ronaghi et al. (2002) Discovery of single nucleotide polymorphisms and mutations by pyrosequencing. Comparative and Functional Genomics, 3:51-56.
Ronaghi et al., "A Sequencing Method Based on Real-Time Pyrophosphate", Science, vol. 281, No. 5375, Jul. 1998, pp. 363-365.
Ronaghi, "Pyrosequencing Sheds Light on DNA Sequencing," Genome Research, 11:3-11 (2001).
Shendure et al., "Next-generation DNA sequencing", Nature Biotechnology, vol. 26, No. 10, Oct. 2008, pp. 1135-1145.
Specification & Drawings of U.S. Appl. No. 61/198,222, filed Nov. 4, 2008.
Svantesson et al., "A mathematical model of the Pyrosequencing reaction system," Biophysical Chemistry, 100:129-145 (2004).
Svantesson, "Mathematical Modelling and Analysis of the Pyrosequencing Reaction System," Dissertation, Universitet Stockholms, Sep. 2005.
U.S. Appl. No. 61/198,222, Appendix to the Specification of U.S. Appl. No. 61/198,222, filed Nov. 4, 2008, 50 pages.

* cited by examiner

SEQUENCE LISTING

<160> NUMBER OF SEQ ID NOS: 2

<210> SEQ ID NO 1
<211> LENGTH: 100
<212> TYPE: DNA
<213> ORGANISM: Artificial Sequence
<220> FEATURE:
<223> OTHER INFORMATION: Description of Artificial Sequence: Ordering of
      Nucleotide Species Flows

<400> SEQUENCE: 1
tacgtacgtc tgagcatcga tcgatgtaca gctacgtacg tctgagcatc gatcgatgta      60
cagctacgta cgtctgagca tcgatcgatg tacagctacg                          100

<210> SEQ ID NO 2
<211> LENGTH: 100
<212> TYPE: DNA
<213> ORGANISM: Artificial Sequence
<220> FEATURE:
<223> OTHER INFORMATION: Description of Artificial Sequence: Ordering of
      Nucleotide Species Flows

<400> SEQUENCE: 2
tacgtacgta cgtacgtacg tacgtacgta cgtacgtacg tacgtacgta cgtacgtacg      60
tacgtacgta cgtacgtacg tacgtacgta cgtacgtacg                          100

METHODS AND APPARATUSES FOR ESTIMATING PARAMETERS IN A PREDICTIVE MODEL FOR USE IN SEQUENCING-BY-SYNTHESIS

RELATED APPLICATIONS

This application is a continuation of U.S. application Ser. No. 13/967,665 filed Aug. 15, 2013, which claims priority to U.S. application No. 61/775,322 filed Mar. 8, 2013, and U.S. application No. 61/684,221 filed Aug. 17, 2012, which disclosures are herein incorporated by reference in their entirety. The U.S. application Ser. No. 13/967,665 is also a continuation-in-part of U.S. application Ser. No. 13/283,320 filed Oct. 27, 2011, which claims priority to U.S. application No. 61/407,377 filed Oct. 27, 2010, which disclosures are herein incorporated by reference in their entirety

SEQUENCE LISTING

The instant application contains a Sequence Listing which has been submitted in ASCII format via EFS-Web and is hereby incorporated by reference in its entirety. Said ASCII copy, created on Nov. 18, 2016, is named LT00316CIP_ST25.txt, and is 1,196 bytes in size.

TECHNICAL FIELD

The present application generally relates to nucleic acid sequencing, and more particularly, to methods for estimating parameters related to a statistical model to estimate signal correction parameters.

BACKGROUND

Sequencing-by-synthesis is among a new generation of high throughput DNA sequencing technologies. Examples of techniques and platforms for sequencing-by-synthesis include the Genome Analyzer/HiSeq/MiSeq platforms (Illumina, Inc.; see, e.g., U.S. Pat. Nos. 6,833,246 and 5,750,341); those applying pyrosequencing-based sequencing methods such as that used by Roche/454 Technologies on the GS FLX, GS FLX Titanium, and GS Junior platforms (see, e.g., Ronaghi et al., SCIENCE, 281:363 (1998) and Margulies et al., NATURE, 437:376-380 (2005)); and those by Life Technologies Corp./Ion Torrent in the PGM™ system (see, e.g., U.S. Patent Application Publication Nos. 2010/0137143 and 2009/0026082, which are incorporated by reference in their entirety). As will be further explained below, one of the problems in sequencing-by-synthesis is the loss of phase synchrony and/or signal droop, which can hinder the ability to make accurate base calls. More accurate estimates of the phasing effects and/or signal droop can improve the ability to make accurate base calls.

BRIEF DESCRIPTION OF THE DRAWINGS

The accompanying drawings illustrate one or more exemplary embodiments of the present invention and serve to explain the principles of various exemplary embodiments. The drawings are exemplary and explanatory only and are not in any way limiting of the present invention.

FIG. 2 discloses SEQ ID NO: 1.

FIG. 3A discloses SEQ ID NO: 2. FIG. 3B discloses SEQ ID NO: 2.

SUMMARY

Figure 1:
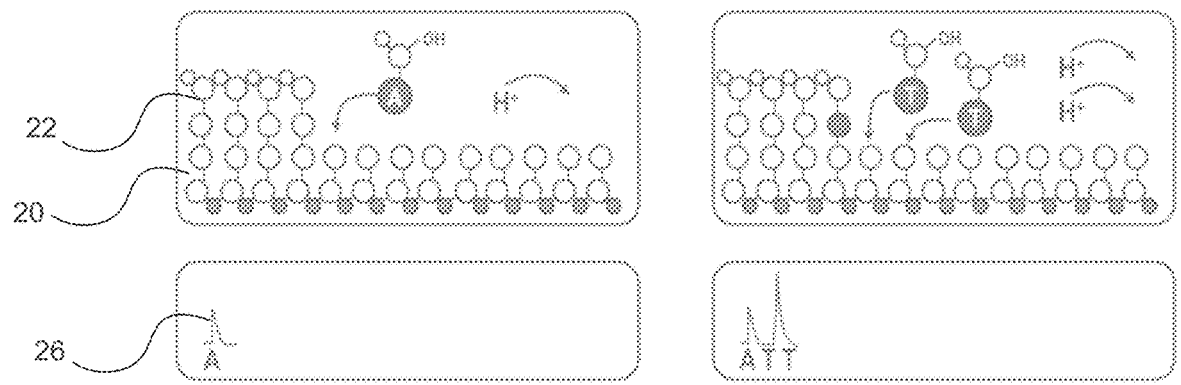
FIG. 1 shows a DNA sample undergoing a sequencing reaction.

In an embodiment, the present teachings provide a method of estimating a parameter related to sequencing of a sample nucleic acid template, comprising: (a) receiving signal data relating to nucleotide incorporation events resulting from a series of flows of nucleotides onto an array of wells including (i) a first well containing the sample nucleic acid template and (ii) a plurality of other sample-containing wells; (b) determining sequence information for the sample nucleic acid template using signal data from the first well; (c) constructing a phase-state model for a set of nucleotide flows that contributed at least in part to the sequence information, wherein the model includes a signal correction parameter that is determined using signal data from the plurality of other sample-containing wells, and wherein the model is stored in a machine-readable memory; (d) calculating, using the phase-state model, predicted signals for the plurality of other sample-containing wells resulting from the set of nucleotide flows; (e) comparing the predicted signals to the signal data from the plurality of other sample-containing wells; (f) fitting the signal correction parameter of the phase-state model based on the comparison of the predicted signals to the signal data from the plurality of other sample-containing wells; and (g) storing the fitted signal correction parameter in the memory.

In an embodiment, the present teachings provide an apparatus comprising: a machine-readable memory; and a processor configured to execute machine-readable instructions, said instructions which when executed cause the apparatus to: (a) receive signal data relating to nucleotide incorporation events resulting from a series of flows of nucleotides onto an array of wells including (i) a first well containing the sample nucleic acid template and (ii) a plurality of other sample-containing wells; (b) determine sequence information for the sample nucleic acid template using signal data from the first well; (c) construct a phase-state model for a set of nucleotide flows that contributed at least in part to the sequence information, wherein the model includes a signal correction parameter that is determined using signal data from the plurality of other sample-containing wells, and wherein the model is stored in a machine-readable memory; (d) calculate, using the phase-state model, predicted signals for the plurality of other sample-containing wells resulting from the set of nucleotide flows; (e) compare the predicted signals for the plurality of other sample-containing wells to the signal data from the plurality of other sample-containing wells; (f) fit the signal correction parameter of the phase-state model based on the comparison of the predicted signals to the signal data from the plurality of other sample-containing wells; and (g) store the fitted signal correction parameter in the memory.

In an embodiment, the present teachings provide a method of sequencing a sample nucleic acid template, comprising: (a) receiving signal data relating to nucleotide incorporation events resulting from a series of flows of nucleotides onto an array of wells including (i) a first well containing the sample nucleic acid template and (ii) a plurality of other sample-containing wells; (b) determining preliminary sequence information for the sample nucleic acid template using the signal data from the first well; (c) constructing a phase-state model for a first set of nucleotide flows that contributed at least in part to the sequence information, wherein the model includes a signal correction parameter fitted by comparing signal data from the plurality of other sample-containing wells to predicted signals for the plurality of other sample-containing wells resulting from the first set of nucleotide flows, and wherein the model is stored in a machine-readable memory; and (d) determining revised sequence information for the sample nucleic acid template by performing a base calling analysis of the signal data from the first well using the signal correction parameter fitted based on signal data from the plurality of other sample-containing wells.

The foregoing summary and following description are exemplary and explanatory only and serve to explain the principles of various exemplary embodiments. Accordingly, the foregoing summary and following description are not in any way limiting of the present invention.

EXEMPLARY EMBODIMENTS

In an embodiment, the present invention provides a method of sequencing a polynucleotide strand, comprising: (a) flowing a series of nucleotides to the polynucleotide strand; (b) obtaining signal data relating to chemical reactions resulting from the flow of nucleotides; (c) determining, using the signal data, sequence information of at least a portion of the polynucleotide strand; (d) constructing a model for a set of flows that encompasses the sequence information, wherein said model includes a signal correction parameter; (e) calculating, using the phase-state model, predicted signals resulting from the set of nucleotide flows; (f) comparing the predicted signals to the signal data; and (g) adjusting the signal correction parameter of the phase-state model based on the comparison of the predicted signals to the signal data. In some cases, the model is a phase-state model that simulates a population of the polynucleotide strands.

In some cases, the nucleotides are flowed onto an array having multiple wells, wherein the polynucleotide strand is contained in a first well of the array, and the method further comprises: obtaining signal data relating to chemical reactions in a plurality of other wells within a region around the first well; and performing steps (c) through (g) for each of the obtained signal data from the plurality of other wells to obtain multiple adjusted signal correction parameters. In some cases, the method further comprises calculating a region-wide estimate of the signal correction parameter using the multiple adjusted signal correction parameters. In some cases, the comparing step comprises calculating a fitting metric that measures the fit between the predicted signals and the signal data from at least some of the plurality of wells. In some cases, the fitting metric measures the fit between the predicted signals and the signal data from less than all of the plurality of wells; wherein the region-wide estimate excludes adjusted signal correction parameters from wells that produce a fitting metric exceeding a predetermined threshold. In some cases, the method further comprises performing a base calling analysis of the signal data from multiple wells within the region using the region-wide estimate of the signal correction parameter.

In some cases, the method further comprises repeating steps (d) through (g) using the adjusted signal correction parameter. In some cases, use of the adjusted signal correction parameter improves the fit between the signal data and the predicted signals. In some cases, calculating the predicted signals uses a signal droop rate as one of the terms. In some cases, the phase-state model includes two or more signal correction parameters, including a carry forward rate and an incomplete extension rate.

In some cases, the comparing step comprises calculating a fitting metric that measures a fit between the predicted signals and the signal data. In some cases, the adjusting step comprises determining a value of the signal correction parameter that optimizes the fitting metric. In some cases, the fitting metric is calculated using only nucleotide flows that result in nucleotide non-incorporation or single nucleotide incorporations. In some cases, the method further comprises performing a base calling analysis of the signal data using the adjusted signal correction parameter.

In some cases, the set of nucleotide flows is a first set of nucleotide flows and the sequence information is a first sequence information, and the method further comprises: applying the phase-state model using the adjusted signal correction parameter; calculating, using the phase-state model, predicted signals resulting from a second set of nucleotide flows that includes nucleotide flows that are not in the first set of nucleotide flows; making base calls by comparing the signal data to the predicted signals; and obtaining a second sequence information about the polynucleotide strand, wherein the second sequence information includes sequence information not contained in the first sequence information. In some cases, the method further comprises repeating steps (d) through (g) using the second sequence information to obtain a further adjusted signal correction parameter.

In some cases, the array includes a chemFET sensor array for detecting a reaction of the nucleotides with the contents of the wells in the array. In some cases, the phase-state model simulates a population of the polynucleotide strands. In some cases, the calculation of the predicted signals includes the use of a signal droop rate. In some cases, the phase-state model is adjusted for the signal droop rate.

In some cases, the region is a first region and the signal droop rate is obtained by a method comprising: receiving signal data relating to chemical reactions in a plurality of wells within a second region of the array, wherein the plurality of wells includes the well containing the polynucleotide strand, wherein the second region is the same or different from the first region; calculating a set of averaged signal values from the signal data; and determining a region-wide signal droop rate by fitting a signal decay function to the set of averaged signal values.

In another embodiment, the present invention provides a non-transitory machine-readable storage medium comprising instructions which, when executed by a processor, cause the processor to perform the above-described methods. In some cases, the processor is caused to: (a) receive signal data relating to chemical reactions resulting from a flow of nucleotides onto an array containing multiple wells, at least one of said wells containing a polynucleotide strand; (b) determine, using the signal data, sequence information of at least a portion of the polynucleotide strand; (c) construct a phase-state model stored in a computer memory, wherein said model is constructed for a set of flows that encompasses the sequence information and includes a signal correction parameter; (d) calculate, using the phase-state model, predicted signals resulting from the set of nucleotide flows; (e) compare the predicted signals to the signal data; (f) adjust the signal correction parameter of the phase-state model based on the comparison of the predicted signals to the signal data; and (g) store the adjusted signal correction parameter in the memory.

In another embodiment, the present invention provides an apparatus comprising: a machine-readable memory; and a processor configured to execute machine-readable instructions, said instructions which when executed cause the apparatus to perform the above-described methods. In some cases, the apparatus is programmed to: (a) receive signal data relating to chemical reactions resulting from a flow of nucleotides onto an array containing multiple wells, at least one of said wells containing a polynucleotide strand; (b) determine, using the signal data, sequence information of at least a portion of the polynucleotide strand; (c) construct a phase-state model stored in the memory, wherein said model is constructed for a set of flows that encompasses the sequence information and includes a signal correction parameter; (d) calculate, using the phase-state model, predicted signals resulting from the set of flows; (e) compare the predicted signals to the signal data; (f) adjust the signal correction parameter of the phase-state model based on the comparison of the predicted signals to the signal data; and (g) store the adjusted signal correction parameter in the memory. In some cases, the apparatus further comprises: a plurality of reservoirs comprising different nucleotide reagents; and a flow chamber for receiving the nucleotide reagents.

In another embodiment, the present invention provides a method of sequencing a polynucleotide strand contained in a well of an array having multiple wells, comprising: flowing a series of nucleotides to the array; receiving signal data relating to chemical reactions in a plurality of wells within a region of the array, wherein the plurality of wells includes the well containing the polynucleotide strand; calculating a set of averaged signal values from the signal data; and determining a region-wide signal droop rate by fitting a signal decay function to the set of averaged signal values.

In some cases, the signal decay function is an exponentially decaying function. In some cases, the method further comprises performing a base calling analysis of the signal data from the well containing the polynucleotide strand using the region-wide signal droop rate. In some cases, the method further comprises: applying the region-wide signal droop rate to the signal decay function; and fitting the signal decay function to the signal data from the well containing the polynucleotide strand to obtain an individual-read signal droop rate. In some cases, the method further comprises performing a base calling analysis of the signal data from the well containing the polynucleotide strand using the individual-read signal droop rate.

In some cases, the method further comprises: constructing a phase-state model to simulate a population of the polynucleotide strands for a set of nucleotide flows, wherein the model includes one or more parameters for incomplete extension rate, carry forward rate, or both; using the phase-state model and the signal droop rate to calculate predicted signals resulting from the set of flows; and performing base calls by comparing the predicted signals to the signal data.

In another embodiment, the present invention provides a non-transitory machine-readable storage medium comprising instructions which, when executed by a processor, cause the processor to perform the above-described methods. In some cases, the processor is caused to: receive signal data relating to chemical reactions in a plurality of wells within a region of a well array that is subjected to the flow of a series of nucleotides; calculate a set of averaged signal values from the signal data; and determine a region-wide signal droop rate by fitting a signal decay function to the set of averaged signal values.

In another embodiment, the present invention provides an apparatus comprising: a machine-readable memory; and a processor configured to execute machine-readable instructions, said instructions which when executed cause the apparatus to perform the above-described methods. In some cases, the apparatus is programmed to: receive signal data relating to chemical reactions in a plurality of wells within a region of a well array that is subjected to the flow of a series of nucleotides; calculate a set of averaged signal values from the signal data; and determine a region-wide signal droop rate by fitting a signal decay function to the set of averaged signal values. In some cases, the apparatus further comprises: a plurality of reservoirs comprising different nucleotide reagents; and a flow chamber for receiving the nucleotide reagents.

FIG. 1 illustrates a simplified example of a base calling process in sequencing-by-synthesis. Specifically, FIG. 1 shows a DNA fragment inside a reaction well as it is undergoing sequencing reactions. Sequencing operations produce signal data used to make base calls of the sequence. There is a template strand 20 that is paired with a growing complementary strand 22. In the left panel, an A nucleotide is added to the reaction well, resulting in a single-base incorporation event which generates a single hydrogen ion. In the right panel, T nucleotides are added to the reaction well, resulting in a two-base incorporation event which generates two hydrogen ions. The signals used for making base calls can be represented in an ionogram, which is a graphical representation of the signals received from the sequencing operations after the raw data signals have been processed. The signal produced by the hydrogen ions are shown as peaks 26 in the ionograms.

Figure 2:
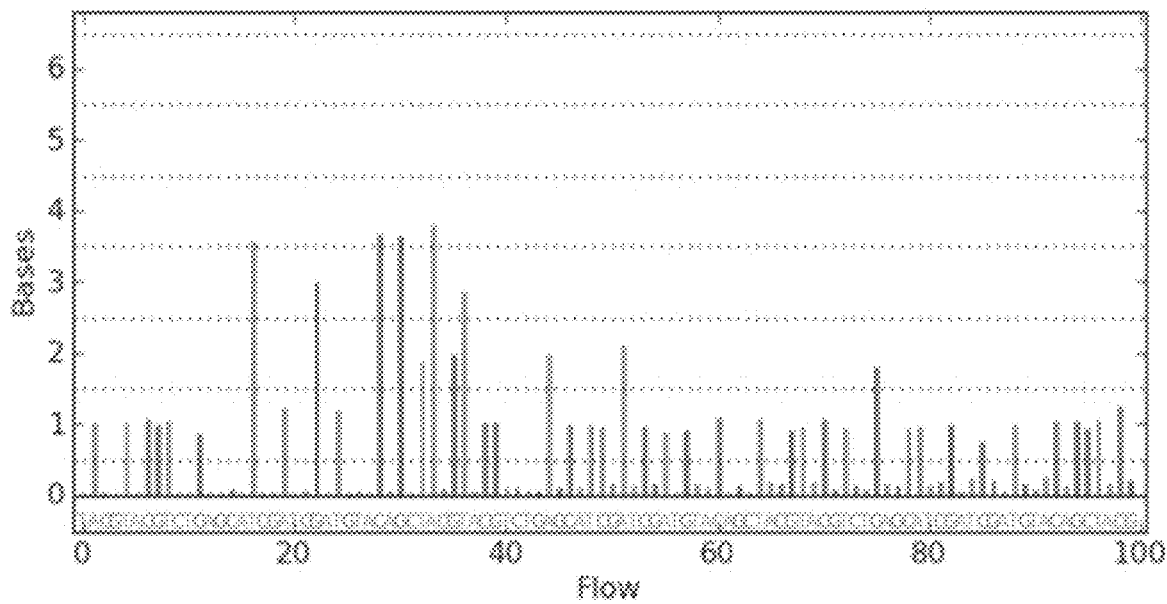
FIG. 2 shows an example of an ionogram from which base calls can be made.

FIG. 2 shows an example ionogram from which base calls can be made. In this example, the x-axis shows the nucleotide species that is flowed and the number of nucleotide bases incorporated can be inferred by rounding to the nearest integer shown in the y-axis.

Figure 3A:
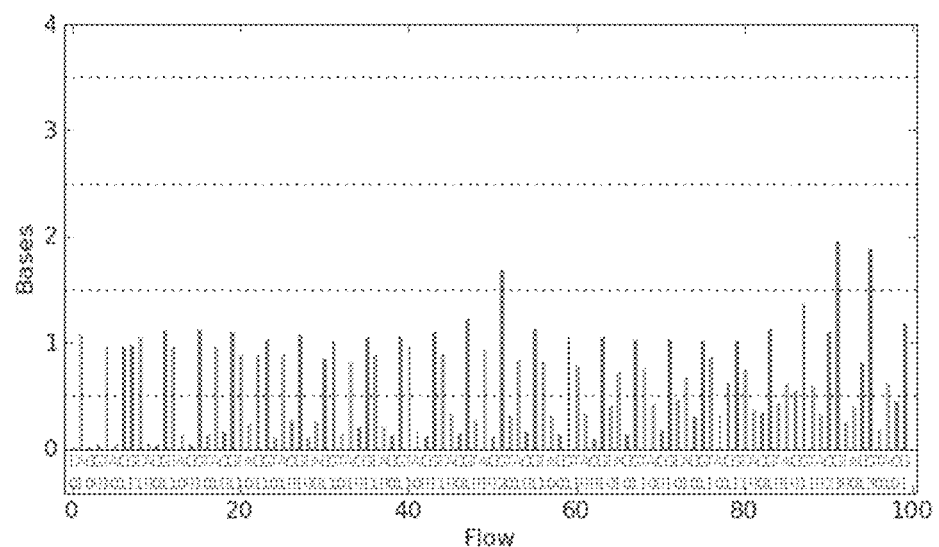
FIG. 3A shows an example of an ionogram for a sequencing read prior to signal correction for phasing effects.
Figure 3B:
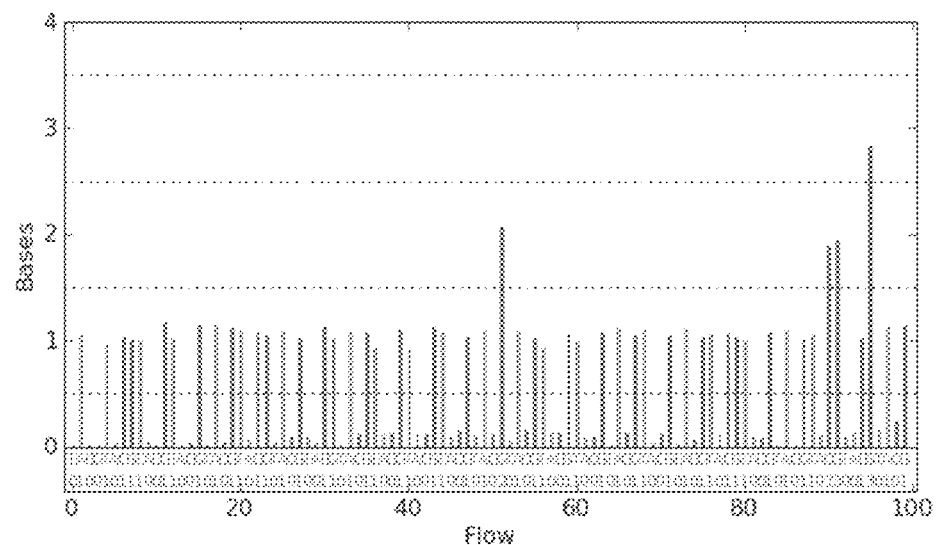
FIG. 3B shows an ionogram for the same sequencing read after signal correction for phasing effects.

Generally, the raw signals received from the sequencing reactions are processed before they are used to make base calls. This signal processing may include making adjustments to the signals to correct for signal droop and phasing effects (as will be explained in more detail below). To demonstrate the effect of phasing correction, FIG. 3A shows an ionogram for a sequencing read prior to signal correction for phasing effects. FIG. 3B shows an ionogram for the same sequencing read after signal correction for phasing effects. More accurate estimates of the phasing effects and/or signal droop can improve the ability to make accurate base calls.

Embodiments of the present invention address the problem of improving the accuracy of base calling in sequencing-by-synthesis of a template polynucleotide strand. The sequencing operations produce measured signal data and this measured signal data is used to make base calls. The signal data used to make the base calls may be taken from any suitable point in the acquisition or processing of the signals received from the sequencing reactions. For example, the signal data may be obtained from the raw signals resulting from the chemical reactions or from a signal obtained after the raw signal has undergone further processing, such as background filtering, normalization, etc. The base calls may be made by analyzing any suitable characteristic of the signal data, such as the signal amplitude (e.g., signal intensity).

Ideally, each extension reaction associated with the population of template polynucleotide strands are performing the same incorporation step at the same sequence position in each flow cycle, which can generally be referred to as being "in phase" or in "phasic synchrony" with each other. However, it has been observed that some fraction of template strands in each population may lose or fall out of phasic synchronism with the majority of the template strands in the population. That is, the incorporation events associated with a certain fraction of template strands may either get ahead of or fall behind other template strands in the sequencing run. Such phase loss effects are described in Ronaghi, GENOME RESEARCH, 11:3-11 (2001); Leamon et al., CHEMICAL REVIEWS, 107:3367-3376 (2007); Chen et al., International Patent Publication WO 2007/098049. Such phasing effects can introduce noise into the signal, thus hindering the ability to make accurate base calls from the signals.

As mentioned above, one cause of phase synchrony loss is the failure of a sequencing reaction to incorporate one or more nucleotide species on a template strand for a given flow cycle may result in that template strand being behind the main template population in sequence position. This effect is referred to as an "incomplete extension" error. Another cause of phase synchrony loss is the improper incorporation of one or more nucleotide species on a template strand may result in that template strand being ahead of the main population in sequence position. This is referred to as a "carry forward" error. Carry forward errors may result from the misincorporation of a nucleotide species, or in certain instances, where there is incomplete removal of a previous nucleotide species in a reaction well (e.g. incomplete washing of the reaction well). Thus, as a result of these phasing effects, at a given flow cycle, the population of template strands may be a mixture of strands in different phase-states. As noted above, the out-of-phase template strands can introduce noise into the signal, making accurate base calling more difficult.

According to exemplary embodiments of the present invention, more accurate estimates of signal correction parameters that can be applied to the signal analysis used for base calling are provided. As used herein, "signal correction parameter" means any parameter that can be applied to the analysis of the measured signal data to account for effects that increase noise, blur the signal, or otherwise affect the signal in such a way to impair the ability to make accurate base calls. Examples of signal correction parameters include phasing effect parameters, such as the incomplete extension rate and the carry forward rate, and signal droop (sometimes also referred to as signal decay).

According to exemplary embodiments of the present invention, these estimates of signal correction parameter(s) may be obtained by using a statistical model of the sequencing process. The model may be constructed in any suitable fashion to mathematically describe the sequencing process. In some cases, the model is a phase-state model that simulates a population of template strands as it undergoes the sequencing process and becomes divided into different phase-states as the sequencing-by-synthesis progresses. The number of template strands in each phase-state may be calculated using one or more phasing effect parameters, such as the incomplete extension rate and/or the carry forward rate.

Each phase-state may represent a template strand having a different number of nucleotide bases incorporated. In other words, template strands in different phase-states have a different number of nucleotide bases incorporated. In some cases, homopolymer incorporations (more than a single incorporation) on homopolymer stretches of the template may be considered to occupy the same state. That is, an n-mer base incorporation would take up one phase-state regardless of whether its length is 1-mer, 2-mer, 3-mer, etc. The term "n-mer" refers to the number of contiguous identical complementary bases that are incorporated into the complementary strand on the template strand. If the next base in the template strand is not complementary to the flowed nucleotide, generally no incorporation occurs and the resulting output signal is sometimes referred to as a "0-mer" output signal.

According to exemplary embodiments of the present invention, the different phase-states of the template population are represented in a phasing matrix, in which the flow cycles are represented on one axis and the different phase-states of the template strands are represented on the other axis. Each entry in this matrix contains a value that is related to the number of template strands that occupy that phase-state at that particular flow cycle. Thus, the phasing matrix gives the portion of the population of clonal template strands that occupy each phase-state, which can be calculated using the incomplete extension rate and/or the carry forward rate.

Since the phase-states of the template will depend on the sequence of the template strand and the nucleotide flow ordering, the model may be constructed based on a given nucleotide flow ordering and at least some sequence information about the template strand. Although the sequencing run may have obtained the signal data for the full read of the template strand, this sequence information used by the model may or may not be the complete sequence of the template strand. For example, this sequence information may only represent a portion of the template strand. In some cases, the sequence information may already be known as the true sequence. In some cases, the sequence may not be known beforehand and a preliminary estimate of the sequence is obtained. For example, a preliminary estimate of the sequence can be obtained by establishing preliminary, naive thresholds for the measured signal data to make preliminary base calls and generate the preliminary sequence information. For example, a measured signal value (after normalization to a key sequence) in the range of 0.5 to 1.5 may be called as a 1-mer, a range of greater than 1.5 up to 2.5 may be called as a 2-mer, and so on. As explained below, this preliminary sequence information may be revised as the signal correction parameter(s) are adjusted to provide more accurate signal analysis.

An example of how a phase-state matrix may be constructed is shown in Table 1A below, which shows a phase matrix that simulates a template population of 100,000 identical strands of DNA. The phase matrix is constructed under the following conditions:
  Incomplete extension rate: 1%
  Carry forward rate: 1%
  Signal droop rate: 0%
  Preliminary DNA sequence information: AGTC (nucleotides incorporate with the complement TCAG)
  Flow order: T-A-C-G-T-A Each entry in the matrix is the number of template strands out of the 100,000 that are in a particular phase-state (the blank entries are zero) after the nucleotide flow occurs. The top row of the matrix shows the flow number and the leftmost column shows the phase-state condition of the template strands. Prior to any nucleotide flows taking place (flow 0 or initial state), each of the 100,000 strands is in phase-state 0. As the flow cycles progress, individual template strands in the population move to different phase-states. The number of strands that appropriately proceed to a subsequent phase-state (e.g. next phase state), or inappropriately fail to proceed to a subsequent phase-state (e.g. incomplete extension error), or inappropriately proceed to a subsequent phase-state (e.g. carry forward error) will depend upon various factors, including the rates of incomplete extension and carry forward errors. In this example, the incomplete extension and the carry forward rate are both set at an initial estimate of 1%.

Table 1B below shows an alternate construction of this phase matrix for the same population of template strands, but taking into account the effects of signal droop. In this case, a signal droop rate of 1% per phase-state change is applied to the phase-state model by reducing each phase-state transition by 1% to represent the effect of signal droop.

TABLE 1A

|  | Initial | Flow 1 (T) | Flow 2 (A) | Flow 3 (C) | Flow 4 (G) | Flow 5 (T) | Flow 6 (A) |
| --- | --- | --- | --- | --- | --- | --- | --- |
| State 0 | 100,000 | 1,000 | 1,000 | 1,000 | 1,000 | 10 | 10 |
| State 1 |  | 99,000 | 99,000 | 990 | 990 | 1,980 | 1,980 |
| State 2 |  |  |  | 97,040 | 97,040 | 97,040 | 970 |
| State 3 |  |  |  | 970 | 10 | 10 | 96,080 |
| State 4 |  |  |  |  | 960 | 960 | 960 |

TABLE 1B (with 1% signal droop rate).

|  | Initial | Flow 1 (T) | Flow 2 (A) | Flow 3 (C) | Flow 4 (G) | Flow 5 (T) | Flow 6 (A) |
| --- | --- | --- | --- | --- | --- | --- | --- |
| State 0 | 100,000 | 1,000 | 1,000 | 1,000 | 1,000 | 10 | 10 |
| State 1 |  | 98,010 | 98,010 | 980 | 980 | 1,960 | 1,960 |
| State 2 |  |  |  | 95,109 | 95,109 | 95,109 | 951 |
| State 3 |  |  |  | 941 | 9 | 9 | 93,225 |
| State 4 |  |  |  |  | 923 | 923 | 923 |

The phase matrix in Table 1B is explained in more detail as follows. In this example, prior to any nucleotide flows taking place (flow 0 or initial state), each of the 100,000 strands is in state 0. In the first flow, the nucleotide species T is flowed. Since this nucleotide species is complementary to the first base in the AGTC template sequence, this should ideally result in the incorporation of the T nucleotide species in all 100,000 strands, which would all move from state 0 to state 1. However, because of the 1% incomplete extension rate, some of the strands remain in the prior state. Also, because of the 1% droop rate, some of the strands are removed from the population to represent this loss. In this case, 99,000 strands advance. However, some of those advancing strands will experience droop (polymerase loss for example) and fail to further incorporate; thus 98,010 strands are now present in state 1, and 1,000 strands (i.e. 1% of the population) remains in state 0.

In the second flow, the nucleotide species A is flowed. Since this nucleotide species is not complementary to the second base in the AGTC template sequence, there is no incorporation event and none of the templates move to phase-state 2. In the third flow, the nucleotide species C is flowed. Since this nucleotide species is complementary to the second base in the AGTC template sequence, this should ideally result in the incorporation of the C nucleotide species in all 98,010 strands in phase-state 1. However, after accounting for the 1% incomplete extension rate and the 1% droop rate, 97,040 strands advance and 970 strands remain in phase-state 1. Moreover, because of the 1% carry forward rate, some of the template strands that advanced into state 2 further advance to phase-state 3. The population is reduced with each advance to represent the loss from signal droop (on a per phase-state change basis). As shown in Table 1B, this process is repeated through flows 4-6 in a cascading fashion to build the phase matrix.

In the fourth flow, the nucleotide species G is flowed. Since this nucleotide species is not complementary to the third base in the AGTC template sequence, there is no incorporation in the main population in phase-state 2. Note however that those template strands that carried forward to phase-state 3 during flow #3 continue to carry forward to phase-state 4 in flow #4 in the matrix shown in Table 1B. In the fifth flow, the nucleotide species T is flowed. Since this nucleotide species is not complementary to the third base in the AGTC template sequence, there is no incorporation in the main population in phase-state 2. Note however that 99% of those template strands that carried forward to phase-state 3 during flow #3 and phase-state 4 during flow #4 continues to carry forward to phase-state 5 in flow #5. Also, the template strands that were in phase-state 0 (due to incomplete extension in flow #1 of the T nucleotide species) have now moved to phase-state 1 with this second flow of the T nucleotide species.

In the sixth flow, the nucleotide species A is flowed. Since this nucleotide is complementary to the third base in the AGTC template sequence, the effect of this incorporation event is shown in Table 1B. In particular, 99% of the template strands that were in phase-state 2 incorporate properly and advance to phase-state 3. Also note that 99% of those strands that carried forward to phase-state 3 during flow #3, phase-state 4 during flow #4, and phase-state 5 during flow #5 continues to carry forward to phase-state 6 in flow #6. Also, with each group of advancing strands, some portion of the population is removed to account for signal droop.

Table 1A shows a similar progression of phase-states, but without accounting for signal droop. In this situation, any signal droop can be factored separately into the calculation for the predicted signals. Since the phase-state model provides a simulation of the phase-state for each strand within the population of templates, this simulation can be used to predict the signals that would be expected if there were nucleotide incorporations, or no incorporation in the next flow. This can be done for a series including 0-mer, 1-mer, 2-mer, and so on, in order to generate a list of predicted signals. These model-predicted signals can be compared against the actually measured signals to fit the model to the measured signal data. Table 2A below shows a comparison of the model-predicted signals and the actual measured signals for the above-described example in Table 1A.

The predicted signal can be calculated in any suitable manner based on the relationship between the signal intensity and the number of nucleotides incorporated. In this example, the predicted signal is proportional to the total number of nucleotide incorporations that occur in that flow, normalized to 100,000 total nucleotide incorporations producing a normalized signal of 1.0000. For example, in Table 1A, there are 97,040 nucleotide incorporations that occur in flow #3 when the template population in state 1 moves to state 2. Additionally, there are 1,940 nucleotide incorporations that occur in flow #3 when 970 of the template strands in state 1 move to state 2, and then move further from state 2 to state 3 because of the 1% carry forward rate. Thus, there are a total of 98,980 nucleotide incorporations that occur in flow #3. When divided by 100,000 for normalization, the predicted signal at flow #3 is calculated to be 0.9898, as shown in Table 2A. The predicted signals in Table 2A can be further adjusted to account for any signal droop. For example, each predicted signal value can be reduced by the amount of signal droop. The predicted signals in Table 2B are generated from the phase matrix of Table 1B, which has already accounted for the signal droop rate. Thus, the predicted signals in Table 2B represent signals that would be expected with the effect of signal droop.

TABLE 2A

|  | Flow 1 (T) | Flow 2 (A) | Flow 3 (C) | Flow 4 (G) | Flow 5 (T) | Flow 6 (A) |
| --- | --- | --- | --- | --- | --- | --- |
| Predicted | 0.9900 | 0.0000 | 0.9898 | 0.0096 | 0.0099 | 0.9607 |
| Measured | 1.0200 | 0.0035 | 1.0049 | 0.0170 | 0.0237 | 0.9804 |

TABLE 2B (with a 1% signal droop rate).

|  | Flow 1 (T) | Flow 2 (A) | Flow 3 (C) | Flow 4 (G) | Flow 5 (T) | Flow 6 (A) |
| --- | --- | --- | --- | --- | --- | --- |
| Predicted | 0.9900 | 0.0000 | 0.9798 | 0.0093 | 0.0099 | 0.9416 |
| Measured | 1.0200 | 0.0035 | 1.0049 | 0.0170 | 0.0237 | 0.9804 |

Any suitable fitting technique can be used to fit the model to the measured signal data, such as maximum likelihood, regression analysis, and Bayesian techniques. In some cases, a fitting metric that measures the fit between the model-predicted signals and the measured signal data can be used for the fitting process. For example, the fitting metric may be the sum of the absolute differences between the measured signals and the model-predicted signals (sum of residual errors) at each flow divided by the number of flows. In another example, the fitting metric may be the square root of the sum of the squared residuals (measured signal−predicted signal). In other examples, weighted coefficients may be applied to the residuals or other properties of the predictions themselves may be used in the calculation of the fitting metric.

The fitting metric can encompass all the nucleotide flows or less than all the nucleotide flows. In some cases, the fitting metric is applied to all the flows that have been modeled or all the flows that encompass the sequence information. In some cases, only a certain range of flows may be considered in the fitting metric, for example, flows numbers 12-60 or flows numbers 12-40. In some cases, certain flows may be excluded. For example, the flows through a key sequence and/or barcode sequence in the template strand may be ignored in the fitting metric (e.g. the first 8 or 12 flows may be excluded). In another example, flows that result in larger homopolymers (e.g. 3-mers or longer) may be ignored. In another example, only flows that result in non-incorporation or single nucleotide incorporations may be considered in the fitting metric.

The model fitting may involve an iterative process of varying one or more signal correction parameters of the phase-state model to improve the fit (e.g. obtaining the best fit by minimizing the residual error sums) between the model-predicted signals and the measured signal data. Any suitable optimization algorithm may be used in the process of finding model parameter(s) that produce predicted signal values having improved fit with the measured signal data, which may include a gradient-descent type algorithm that varies the signal correction parameter(s) of the model until they converge on the solution with the minimal residual error.

This fitting step may result in an improved estimate of the signal correction parameter(s). In a microwell array, there are many wells that contain template strands that undergo simultaneous or parallel sequencing. As such, there may be multiple reads available for obtaining improved estimates of the signal correction parameter(s). In other words, when sequencing on a microwell array, there may be multiple sets of measured signal data, each representing a read from one of the multiple wells of the microwell array. In such instances, the above-described process may be applied to other sets of measured signal data to obtain additional estimates for signal correction parameter(s).

In some cases, the fitted signal correction parameter(s) may be obtained for each individual well read and be applied to the measured signal data for that individual well only. Alternatively, in some cases, regional estimates may be taken where the fitted signal correction parameter(s) from multiple individual wells in a selected region of the microwell array (e.g. a region size of 100×100 wells) are taken and statistically analyzed to obtain a region-wide estimate of the parameter(s). The signal data from the group of wells may be subject to any suitable statistical analysis to obtain a single value as a region-wide estimate that quantitatively summarizes the collection of signal data, including calculating an average, a weighted average, some function of the average, a mean, or a mode of the signal data.

This region-wide estimate of the parameter(s) may also be further refined. In some cases, sequence reads that produce poorly fitting measured signal data may be excluded from the calculation of the region-wide estimate. For example, reads with high residual errors in the fitting (e.g. exceeding a maximum residual error threshold) or those that are poorly fitting (e.g. exceeding a boundary condition) may be excluded from the calculation of the region-wide estimate.

In some cases, the estimated signal correction parameter(s) may be subject to further statistical refinement. For example, a truncated mean of the multiple estimates may be taken, in which any value outside of a certain threshold range around the calculated mean (e.g. outside a 60% window around the calculated mean) is excluded from the group and the average is recalculated. In some cases, the quality of the individual well reads may be considered in whether to include the individual read in the region-wide estimate. For example, lower quality reads may be excluded, such as mixed reads (i.e. reads from wells containing more than one kind of template strand).

Another problem that can hinder accurate base calling in sequencing-by-synthesis is the decay of the signal (often referred to as signal droop). There are a number of possible reasons for decay of the signal, including loss of DNA polymerase activity, template strands that are unable to incorporate any more nucleotides, washing out of the polymerase or template strands, loss in sensitivity of the well sensors, etc. The signal droop rate can be given in any suitable unit basis, including per flow, per nucleotide incorporation, or per phase-state change.

In another aspect, the present teachings provide a method for obtaining a more accurate estimate of signal droop rate. In some cases, the signal droop rate may be modeled as a decaying function, such as a linearly decaying function or an exponentially decaying function. An example of an exponentially decaying function that can be used for estimating signal droop is expressed by the following equation:

$$S_e(N) = S_b(1-Dpf)^N$$

where $S_e$ is the expected signal at a given flow N; $S_b$ is the baseline signal; Dpf is the signal droop per flow; and N is the flow number. This equation can be solved for signal droop rate as a per-flow decay. To obtain an estimate of signal droop rate on a per-nucleotide incorporation basis, the per-flow droop rate can be divided by the baseline signal.

By varying the signal droop rate parameter, the signal decay function may be fitted to the measured signal data to obtain a more accurate estimate of the signal droop rate. In some cases, the signal decay function may be fitted to an average of the measured signal data taken from multiple wells in a region of the microwell array (e.g. a region size of 100×100 wells). On a microwell array where different wells may contain different fragments of a genome, only some of the fragments will undergo an incorporation for a given flow. But because the different genomic fragments may be considered a random sampling of nucleotide bases at a given flow, regional averages may be useful for fitting the signal decay function.

The fitting of the signal droop rate may encompass all the nucleotide flows or less than all the nucleotide flows. In some cases, only a certain range of flows may be considered in the fitting. In some cases, certain flows may be excluded. For example, the flows through a key sequence and/or barcode sequence in the template strand may be ignored in the fitting because these sequences may not represent diverse or random sequences.

For example, in a typical genome, the probability that the next flow will be a complementary match to the next base in the template stand is 0.333. Moreover, the probability that the next base is a 1-mer, 2-mer, 3-mer etc can also be estimated. Given these two estimates, the average signal measured in a given nucleotide flow for a random population of sequencing templates can then be estimated by the following equation: average signal=P1×Pb×S1+P2×Pb×S2+P3×Pb×S3+ . . . ; where S1, S2, S3 are the strengths of the signals received for 1-mer, 2-mer, 3-mer etc. incorporations, respectively; P1, P2, P3 are the probabilities that for the given incorporation, that incorporation is a 1-mer, 2-mer, 3-mer, etc. respectively; Pb is the probability that the next nucleotide flow matches the next base in the template (i.e. the probability that an incorporation event will occur).

This equation can be rewritten as follows: average signal=Pb×(P1×S1+P2×S2+P3×S3+ . . . ). Given a repeated flow ordering of T-A-C-G, for example, Pb must be ⅓ because during the prior nucleotide flows, one of the flowed nucleotides would have incorporated and a repeated flow of the same nucleotide would not cause an incorporation. Thus, only 3 nucleotide species remain as possible incorporating nucleotides. Therefore, the average signal measured in a nucleotide flow is the sum of the signal received for a 1-mer incorporation (S1) times the probability that the next base will incorporate as a 1-mer (P1), plus the probability that the next base will incorporate as a 2-mer (P2) times the signal generated for that 2-mer (S2; signal is twice a 1-mer when a 2-mer incorporates), plus the probability that the next base will incorporate as a 3-mer times the signal generated for that 3-mer, etc.

Using the foregoing calculations, the expected average of the measured signals for any given flow over many random sequences may be about 0.6. This estimated average of 0.6 is not critical, but this example provides a basis for illustrating the concept of signal droop. Here, 0.6 is the baseline signal (denoted as $S_b$ above) expected before any signal decay has occurred. Tracing the region-wide average signal over successive flows produces a curve that depicts the decay of the signal. Fitting the signal decay function to this curve (by varying the signal droop rate parameter) can produce an improved estimate of the signal droop rate.

Any suitable statistical technique or optimization algorithm may be used to fit the signal decay function to the averaged signal values. The signal droop rate can be provided as a per-region estimate or a per-read estimate (i.e. the read from an individual well). Although the per-region estimates can be obtained faster and more easily, a per-read estimate can be more accurate. As such, in some cases, a per-region estimate can be used as an initial guess of the actual per-read droop. Then, this initial guess can be used in the fitting to obtain a per-read estimate. By starting with a good initial guess, the fitting can converge to an accurate solution more rapidly with less susceptibility to converging on local minima.

After the fitted signal correction parameter(s) are obtained, they can be applied to the signal analysis process that results in base calling. Where a region-wide estimate of the signal correction parameter(s) is used, that region-wide estimate may be applied to the reads (e.g. all the reads) in that particular region. In some cases, the signal correction parameter(s) can be applied to the measured signal data to produce corrected signal data. The corrected signal data can then be used for making base calls. In such cases, any of various types of signal correction techniques may be used for the base calling. For example, the signal correction may be performed using the technique described in H. Eltoukhy & A. El Gamal, "Modeling and Base-Calling for DNA Sequencing-By-Synthesis," at 2006 IEEE International Conference on Acoustics, Speech, and Signal Processing (May 2006). In another example, the signal correction may involve the use of the technique described in U.S. Patent Application Publication No. 2010/0192032 (Chen et al.; 454 Life Sciences Corp.), which is incorporated by reference herein.

In some cases, the signal analysis for base calling may involve using the above-described phase-state model in a predictive mode where, for a given flow, one or more predicted signal values are generated. Since they are calculated from the phase-state model, the predicted signal value(s) are the signal values that would be expected after correcting for phasing effects and/or signal droop. Having these predicted signal values at different flows, base calls can be made by comparing the actually measured signal at a particular flow against the predicted signal value at the same flow.

In some embodiments, multiple predicted signal values can be generated for each flow being considered, each of the predicted signal values being associated with a potential incorporation event (including non-incorporation) that could occur at that flow. For example, Table 3 below shows a list of multiple predicted signal values across several flows over the preliminary sequence information AGTC described above with respect to Table 1. At each flow, there are predicted signal values for a non-incorporation event and the predicted signal values for n-mer incorporations (up to 7-mers). Since the list of predicted signal values encompass multiple possible incorporation events, these predictions can be applied to unknown sequences to make base calls. In this example, the set of predictions is up to 7-mer incorporations per nucleotide flow, but this is for illustration purposes only and does not limit any particular aspect of the present teachings in general. In practice, predicted values can be generated for any number of polymer incorporations (e.g. predictions for 8-mer incorporations, 9-mer incorporations, and so on). The bolded entries in Table 3 indicate the best match against the measured signal data and indicate the incorporation event for the given flow.

TABLE 3

|  | 0-mer | 1-mer | 2-mer | 3-mer | 4-mer | 5-mer | 6-mer | 7-mer |
|---|---|---|---|---|---|---|---|---|
| Flow 1 (T) | 0.0000 | 0.9900 | 1.9800 | 2.9700 | 3.9600 | 4.9500 | 5.9400 | 6.9300 |
| Flow 2 (A) | 0.0000 | 0.9801 | 1.9602 | 2.9403 | 3.9204 | 4.9005 | 5.8806 | 6.8607 |
| Flow 3 (C) | 0.0097 | 0.9898 | 1.9699 | 2.9500 | 3.9301 | 4.9102 | 5.8903 | 6.8704 |
| Flow 4 (G) | 0.0096 | 0.9703 | 1.9310 | 2.8917 | 3.8524 | 4.8131 | 5.7738 | 6.7344 |
| Flow 5 (T) | 0.0099 | 0.9609 | 1.9119 | 2.8629 | 3.8139 | 4.7649 | 5.7158 | 6.6668 |
| Flow 6 (A) | 0.0000 | 0.9607 | 1.9214 | 2.8821 | 3.8428 | 4.8035 | 5.7641 | 6.7248 |

In this example, the signal values are assumed to be generally proportional to the amount of nucleotides incorporated. Thus, for each flow, each predicted signal value associated with a multiple nucleotide incorporation (greater than 1) is calculated as the predicted signal from a single nucleotide incorporation multiplied by the number of incorporations. Thus, each predicted signal value for multiple n-mer (greater than 1) incorporations is calculated using the following equation: $P(n\text{-mer}) = B + (D \times n\text{-mer})$, where $P(n\text{-mer})$ is the predicted signal for the homopolymer n-mer, $B$ is the baseline 0-mer signal value, and $D$ is the signal value for a single nucleotide incorporation (which is the difference in the 1-mer and 0-mer signals, not the absolute predicted 1-mer signal). For example, at flow number 3, $P(2\text{-mer}) = 0.0097 + (0.9898 - 0.0097) \times 2 = 1.9699$. Given a list of predicted signal values for each potential incorporation event, the actually measured signal at that flow can be compared against the predicted signal values and the incorporation event associated with the predicted signal value that most closely matches the measured signal value is made as the base call for that flow cycle.

As a result of this process, more accurate sequence information about the template strand may be obtained. For example, if the preliminary sequence information was based on naïve thresholding, this preliminary sequence can be revised based on analysis of the same measured signal data with improved signal correction parameter(s). Thus, the sequence information may be revised, updated, and/or extended over a greater length with successive iterations of this algorithm.

In some embodiments, the above-described algorithm can be repeated to obtain further, more accurate estimates of the signal correction parameter(s). In some cases, subsequent passes of the iterative process may use a larger set of flows encompassing more of the template strand. For example, if the preliminary sequence information was obtained for only a portion of the template polynucleotide strand, then this algorithm may be repeated for a slightly larger portion of the template strand (and its associated nucleotide flows) to obtain further estimates of the signal correction parameter(s). Also, this iterative process can continue until a sufficient level of confidence in the accuracy of the base calls is achieved. For example, this iterative fitting and re-fitting process over incrementally larger sets of flows can continue until about 100 flows. After this has been repeated for the desired number of flows (e.g. 100 flows), the final signal correction parameter(s) can then used to solve all flows in the manner described above.

For example, the phase-state model may be applied multiple times to the measured signal data. In the first pass, the measured signal data is compared against naïve thresholds to generate an initial guess for the sequence of a portion of the template strand (e.g. the first N bases). In the first pass, the phase-state model may be used with only the effect of incomplete extensions being considered. In subsequent passes, the phase-state model may consider both the effects of incomplete extensions and carry forward effects.

Figure 4:
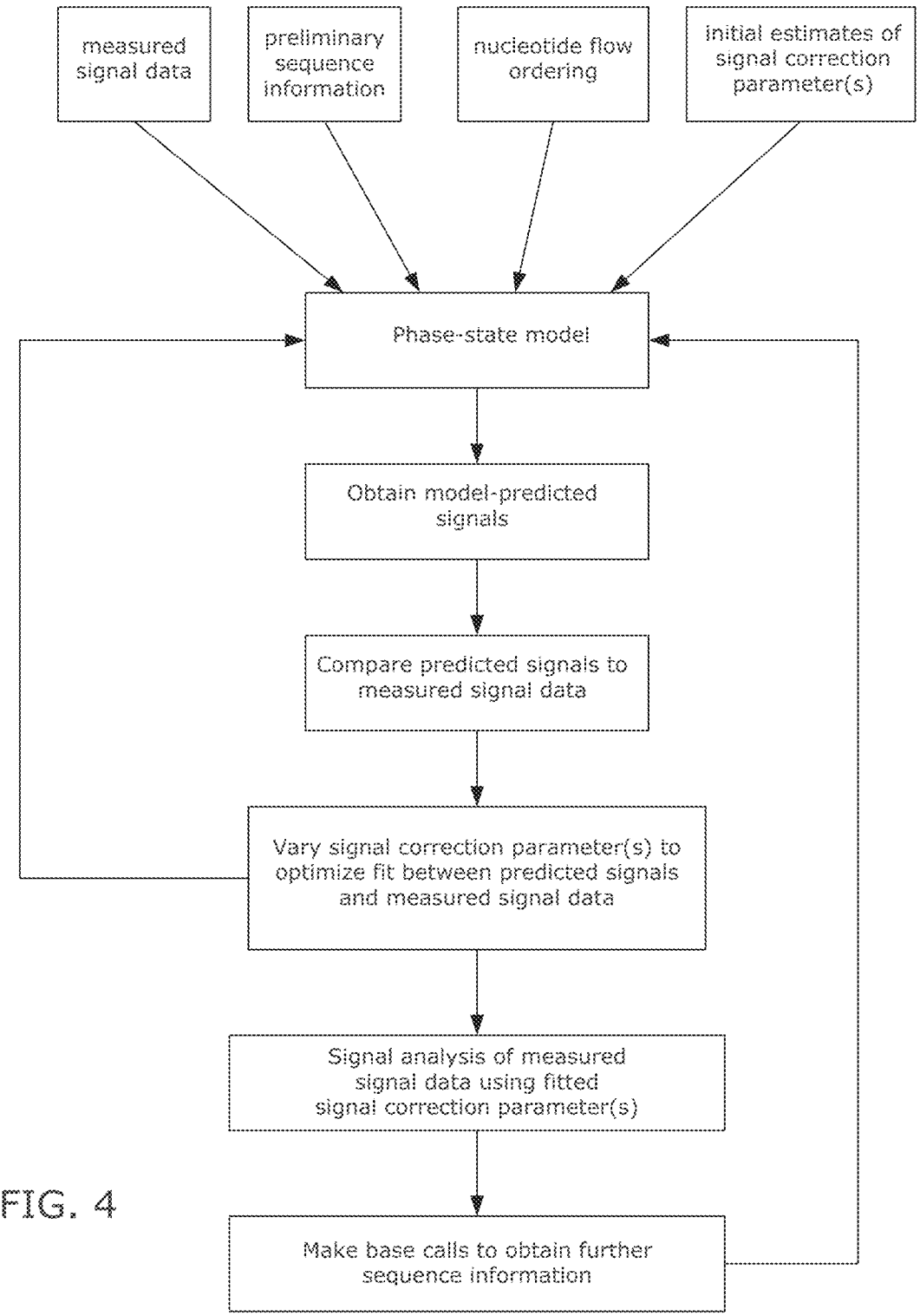
FIG. 4 shows a flow chart illustration of an embodiment of the present invention.

A flow chart illustration of an embodiment of the present teachings is shown in FIG. 4. The measured signal data, the preliminary sequence information (e.g. obtained by base calling using naïve thresholds), the nucleotide flow ordering, and one or more signal correction parameters (e.g. carry forward, incomplete extension, and/or signal droop) are used as inputs to the phase-state model. From the template populations simulated in the model, the predicted signal values over the preliminary sequence information are calculated. The predicted signal values are compared against the measured signal data. In an iterative process, the signal correction parameter(s) are varied and applied as input to the phase-state model until the desired level of optimized fit (e.g. best fit) between the predicted signal values and the measured signal data is achieved. Using the fitted signal correction parameter(s), the measured signal data is analyzed to make base calls that revise, update, and/or extended the sequence information. This new sequence information can be applied to the phase-state model for further iterative passes of the algorithm.

Figure 5:
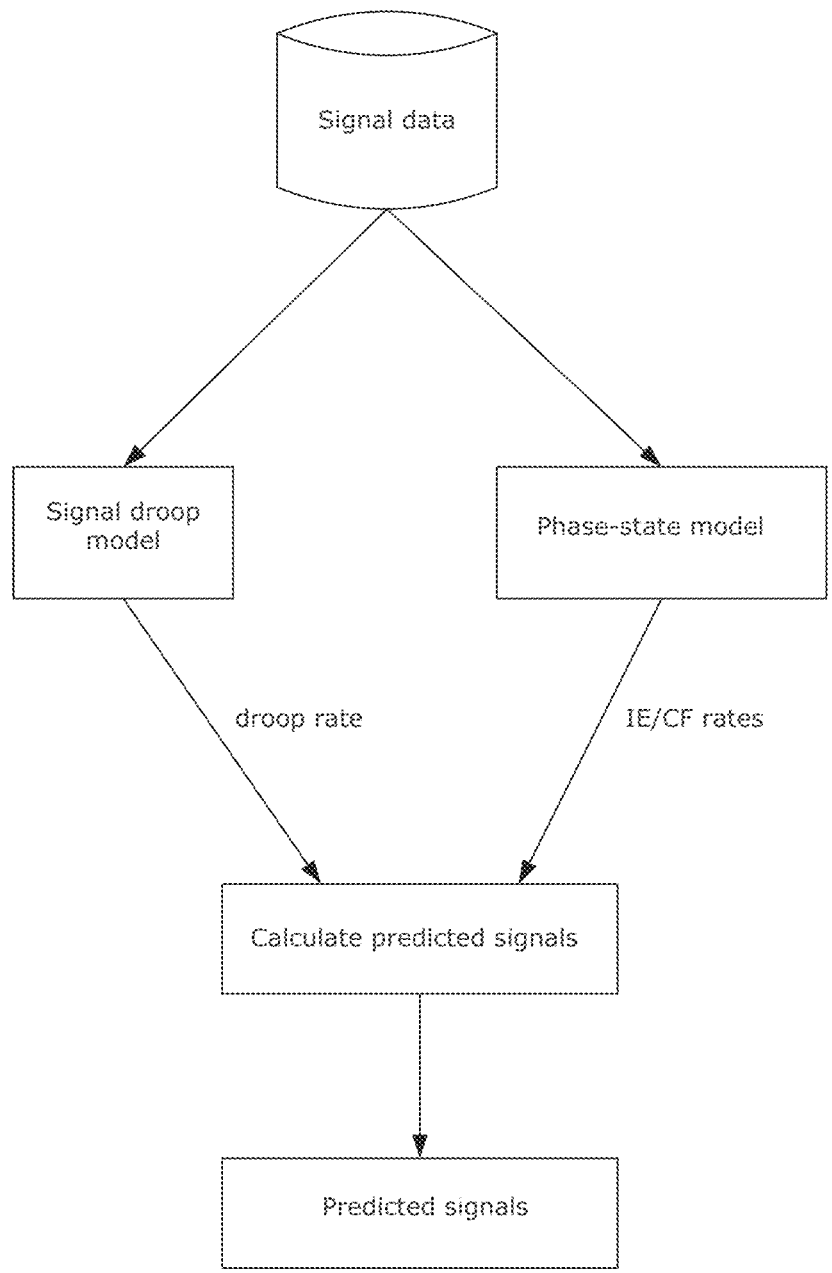
FIG. 5 shows a flow chart illustration of another embodiment of the present invention.

In some cases, the signal droop rate is determined independently from the phasing parameter(s), and in some cases, the same data set may be used in the independent determinations. As explained above, in some cases, the signal droop rate and the phasing parameter(s) may be applied separately to calculate the predicted signals. For example, in the embodiment shown in FIG. 5, a signal droop model is used to calculate a signal droop rate and a phase-state model is used to calculate the rates of incomplete extension (IE) and carry forward (CF). Both models are applied to the signal data and may use the same or different portions of the signal data. Outputs from both models may be used to generate the set of predicted signals. Alternatively, as explained above, the phase-state model itself can be adjusted for the signal droop rate (e.g. by applying reductions on a per phase-state change basis). In this case, the output of the phase-state model alone may be used to calculate the predicted signals.

According to various exemplary embodiments, one or more estimates of one or more signal correction parameters pertaining to any of the various exemplary embodiments described herein may be determined using information obtained from collections or groupings of reaction areas or wells rather than from just individual reaction areas or wells. In certain embodiments, it may be desirable to apply signal correction parameter estimates from one or more reactions areas or wells that are separate or discrete from other reaction areas or wells under analysis. For example, signal correction parameters can be obtained in a manner so that measurements and/or data obtained from reaction areas or wells surrounding or located in proximity to a selected one or more wells (or a selected one or more populations of nucleic acid templates present therein) are determined and applied to the selected one or more wells. Thus the signal correction parameters may be determined and applied without strict dependency on or use of the selected one or more wells in the determination of the signal correction parameter estimates. Aggregate signal correction parameters obtained in this manner may desirably help to avoid or minimize the effect of spurious or errant information that might otherwise undesirably skew the signal correction parameter determination. For example, signal correction parameters may be obtained from an averaging of data obtained from a collection of reaction areas or wells that may or may not include one or more selected reaction areas or wells for which the signal correction parameters are to be applied.

In an exemplary embodiment, the one or more estimates or signal correction parameter determinations may be obtained using regional estimates that may be taken from multiple individual wells (or related populations of nucleic acid templates present therein) in a selected region of a microwell array (e.g., a region size of 100×100 wells, each or some of which containing a population of nucleic acid templates). In an exemplary embodiment, such multiple individual wells may be selected to exclude a particular well (or population of nucleic acid templates present therein) to which signal correction is to be applied (e.g., one or more regional estimates obtained from a given set of wells may be used to correct a signal related to some other well that is not included in the given set of wells used to obtain the one or more regional estimates). By ensuring that signal correction parameters for a given well are determined without directly using the signal from that well, but instead from other wells (e.g., nearby wells), one may avoid overfitting these parameters to any signal artifacts unaccounted for by the signal model.

In another exemplary embodiment, one or more signals for one or more wells may be corrected such that for every given well to which correction is applied, one or more signal correction parameters intended for that given well (such as, e.g., incomplete extension and/or carry forward rate parameters) are obtained from a regional estimate obtained from a set of wells generally surrounding (or located in an area relatively close or otherwise expected to be similar, under some suitable measure, to the area of the given well), but excluding, that given well. In an exemplary embodiment, one or more signals for one or more wells may be corrected such that for every given well to which correction is applied, one or more signal correction parameters intended for that given well (such as, e.g., incomplete extension and/or carry forward rate parameters) are obtained from a regional estimate obtained from two or more classes of wells selected from a set of wells generally surrounding (or located in an area relatively close or otherwise expected to be similar, under some suitable measure, to the area of the given well), but excluding, that given well. In an exemplary embodiment, the two or more classes of wells in such a set of wells may include, for example, classes of wells defined by two or more labels within the population (e.g., 'odd' wells vs. 'even' wells or any other type of label allowing differentiation between wells) or classes of wells defined by inclusion into some defined physical location (e.g., wells that are to the left and right, respectively, of some dividing line or any other type of spatial classification). In an exemplary embodiment, the signal data from the set of wells may be subject to any suitable statistical analysis to obtain a single value as a region-wide estimate that quantitatively summarizes the collection of signal data, including calculating an average, a weighted average, some function of the average, a mean, or a mode of the signal data.

Figure 9:
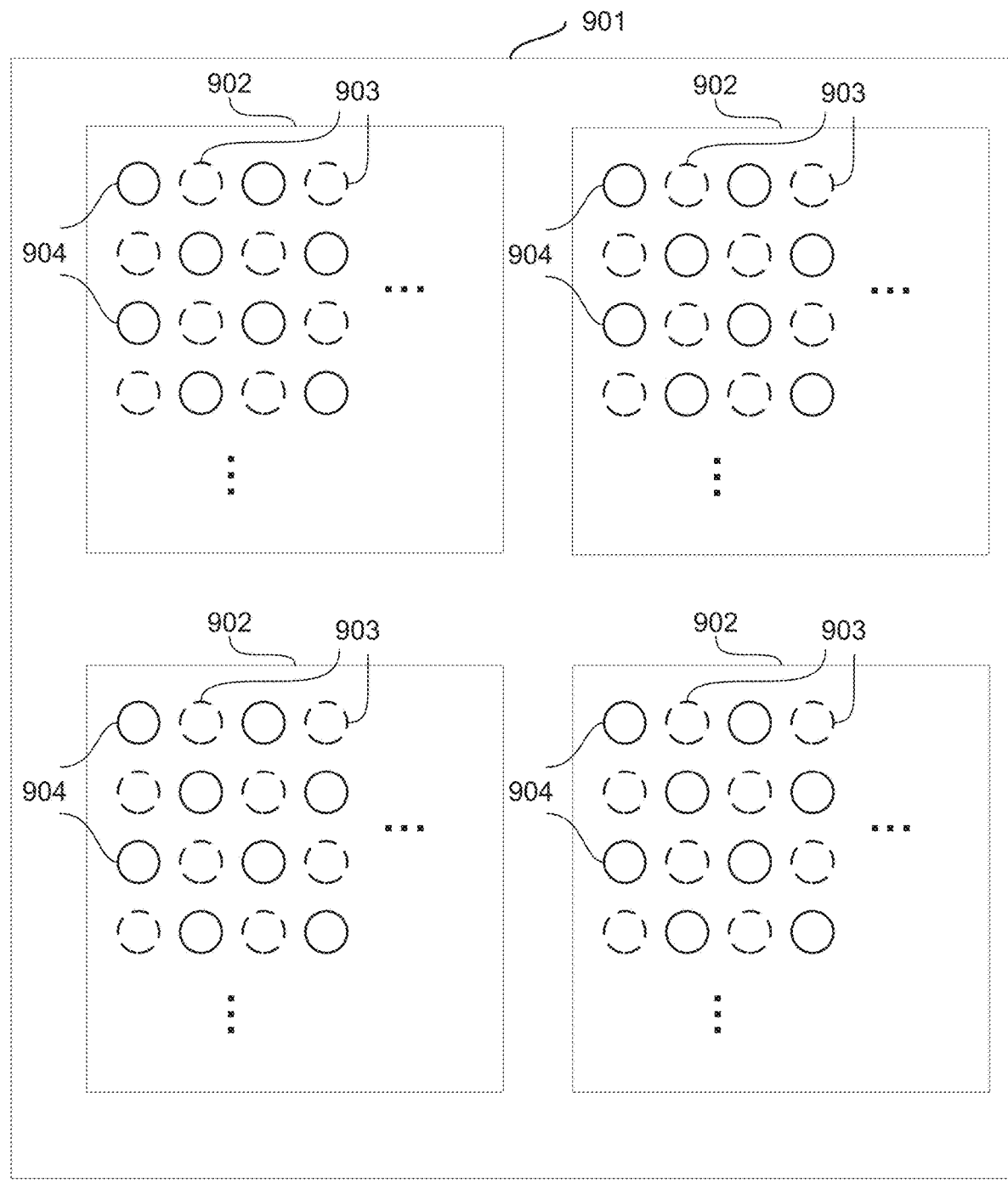
FIG. 9 shows a sensor array including a plurality of sensor regions or subgroups.

FIG. 9 shows a sensor array 901 including a plurality of regions or subgroups 902 of reaction areas or wells. In an embodiment, each region or subgroup 902 includes at least two sets of reaction areas or wells 903 and 904. The sets of reaction areas or wells 903 and 904 may be physically distinguishable from each other (e.g., by shape, dimensions, or inclusion into some defined physical location such as wells that are to the left and right, respectively, of some dividing line or any other type of spatial classification such as a "checkerboard"-type arrangement, or any other physical attribute) and/or they may be distinguishable on the basis of some arbitrary classification that may depend on position or some labeling in software (e.g., "odd" wells versus "even" wells or any other type of label allowing differentiation between wells). In an embodiment, both sets of reaction areas or wells 903 and 904 include a population of template nucleic acids. Each of reaction areas or wells 903 may contain a different population of template nucleic acids, or they may all contain a similar population of template nucleic acids. In some cases, some of reaction areas or wells 903 may be empty. Each of reaction areas or wells 904 may contain a different population of template nucleic acids, or they may all contain a similar population of template nucleic acids. In some cases, some of reaction areas or wells 904 may be empty. In various embodiments, data obtained from some or all of the reaction areas or wells 903 may be used to estimate one or more parameters related to nucleic acid sequencing (e.g., using any parameter estimation embodiment described in the present specification, or another suitable parameter estimation approach), and the one or more parameters so obtained may then be used with and/or applied to process and/or analyze data obtained from some or all of the reaction areas or wells 904 (e.g., using any parameter use embodiment described in the present specification or another suitable parameter use approach). Conversely, data obtained from some or all of the reaction areas or wells 904 may be used to estimate one or more parameters related to nucleic acid sequencing (e.g., using any parameter estimation embodiment described in the present specification, or another suitable parameter estimation approach), and the one or more parameters so obtained may then be used with and/or applied to process and/or analyze data obtained from some or all of the reaction areas or wells 903 (e.g., using any parameter use embodiment described in the present specification or another suitable parameter use approach). In an example, a sensor array may contain many distinct regions of reaction areas or wells (e.g., 64), each region may in turn comprise two groups of reaction areas or wells (e.g., "odd-numbered" and "even-numbered" wells), and a subset of each of these two groups (e.g., 5000 wells in each) may be used to estimate one or more parameters (e.g., incomplete extension rate, carry forward rate, and/or droop rate) for each region, with the one more parameters from the "odd-numbered" group being for use with or application to the "even-numbered" group and vice-versa. In an embodiment, the subsets of wells selected for parameter estimation may to used to estimate the parameters via a suitable optimization algorithm. In various embodiments, the optimization algorithm may include defining an objective function that assigns to every set of parameter values a single scalar measure of dissimilarity between an observed signal and a model-predicted signal in all "training" wells and signals. In various embodiments, such an objective function may be a sum of squares, a mean square error, a L1 norm of a vector difference, etc., or some other suitable objective. In various embodiments, the optimization algorithm may subsequently include performing parameter estimation by minimizing the objective function over the multidimensional space of possible parameter values (e.g., incomplete extension rate, carry forward rate, and/or droop rate), which may be done, for example, using iterative algorithms such as Nelder-Mead, Gauss-Newton, conjugate gradient, or Levenberg-Marquadt.

According to an embodiment, there is provided a method of estimating a parameter related to sequencing of a sample nucleic acid template. In the method, signal data relating to nucleotide incorporation events resulting from a series of flows of nucleotides onto an array of wells are received. The array of wells may include (i) a first well containing the sample nucleic acid template and (ii) a plurality of other sample-containing wells. Sequence information for the sample nucleic acid template may then be determined using the signal data from the first well. Then, a phase-state model for a set of nucleotide flows that contributed at least in part to the sequence information may be constructed, and the model may include a signal correction parameter that is determined using signal data from the plurality of other sample-containing wells. The model may be stored in a machine-readable memory. Then, predicted signals for the plurality of other sample-containing wells resulting from the set of nucleotide flows may be calculated using the phase-state model. The predicted signals may then be compared to the signal data from the plurality of other sample-containing wells. The signal correction parameter of the phase-state model may then be fitted based on the comparison of the predicted signals to the signal data from the plurality of other sample-containing wells. Finally, the fitted signal correction parameter may be stored in the memory.

According to an embodiment, there is provided a method of estimating a parameter related to sequencing of a sample nucleic acid template, comprising: (a) receiving signal data relating to nucleotide incorporation events resulting from a series of flows of nucleotides onto an array of wells including (i) a first well containing the sample nucleic acid template and (ii) a plurality of other sample-containing wells; (b) determining sequence information for the sample nucleic acid template using signal data from the first well; (c) constructing a phase-state model for a set of nucleotide flows that contributed at least in part to the sequence information, wherein the model includes a signal correction parameter that is determined using signal data from the plurality of other sample-containing wells, and wherein the model is stored in a machine-readable memory; (d) calculating, using the phase-state model, predicted signals for the plurality of other sample-containing wells resulting from the set of nucleotide flows; (e) comparing the predicted signals to the signal data from the plurality of other sample-containing wells; (f) fitting the signal correction parameter of the phase-state model based on the comparison of the predicted signals to the signal data from the plurality of other sample-containing wells; and (g) storing the fitted signal correction parameter in the memory.

In various embodiments, the plurality of other sample-containing wells may be disposed in a region generally surrounding the first well. The plurality of other sample-containing wells may also be disposed in a region disparately located from the first well. The plurality of other sample-containing wells may also be disposed in a plurality of different regions. The signal correction parameter may be obtained using signal data obtained from the plurality of other sample-containing wells without using signal data obtained from the first well. The signal correction parameter may also be obtained using both signal data obtained from the plurality of other sample-containing wells and signal data obtained from the first well.

In various embodiments, the method may further comprise: performing steps (b) through (g) for each of the obtained signal data from each or some of the plurality of other sample-containing wells to obtain multiple fitted signal correction parameters, wherein each of the multiple fitted signal correction parameters is determined for a given well without using signal data from that given well. The method may further comprise calculating one or more region-wide estimates of the signal correction parameter using the multiple fitted signal correction parameters. The comparing step may comprise calculating a fitting metric that measures the fit between the predicted signals and the signal data. The fitting metric may measure the fit between the predicted signals and the signal data; and a region-wide estimate may exclude fitted signal correction parameters from wells that produce a fitting metric exceeding a predetermined threshold. The method may further comprise performing a base calling analysis of the signal data from multiple wells within the region using the one or more region-wide estimates of the signal correction parameter. The method may further comprise repeating steps (c) through (g) using the fitted signal correction parameter. Base calling may be performed using any suitable base calling method, including for example as described in Sikora et al., U.S. patent application Ser. No. 13/588,408, filed Aug. 17, 2012, and in Sikora et al., U.S. patent application Ser. No. 13/645,058, filed Oct. 4, 2012, which are incorporated by reference herein in their entirety.

In various embodiments, the phase-state model may include two or more signal correction parameters, such as, e.g., a carry forward rate and/or an incomplete extension rate. The comparing step may comprise calculating a fitting metric that measures a fit between the predicted signals and the signal data. The fitting step may comprise determining a value of the signal correction parameter that optimizes a fitting metric. The fitting metric may be calculated using only nucleotide flows that result in nucleotide non-incorporation or single nucleotide incorporations. The fitting step may comprise determining a value of the signal correction parameter using Nelder-Mead optimization.

In various embodiments, the method may further comprise performing a base calling analysis of the signal data using the fitted signal correction parameter. The set of nucleotide flows may be a first set of nucleotide flows and the sequence information may be a first sequence information, and the method may further comprise: applying the phase-state model using the fitted signal correction parameter; calculating, using the phase-state model and the fitted signal correction parameter obtained using signal data from the plurality of other sample-containing wells, predicted signals for the first well resulting from a second set of nucleotide flows that includes nucleotide flows that are not in the first set of nucleotide flows; making base calls by comparing the signal data from the first well to the predicted signals for the first well; and obtaining a second sequence information about the sample nucleic acid template, wherein the second sequence information includes sequence information not contained in the first sequence information. Base calling may be performed using any suitable base calling method, including for example as described in Sikora et al., U.S. patent application Ser. No. 13/588,408, filed Aug. 17, 2012, and in Sikora et al., U.S. patent application Ser. No. 13/645,058, filed Oct. 4, 2012, which are incorporated by reference herein in their entirety. The method may further comprise repeating steps (d) through (g) using the second sequence information to obtain a further fitted signal correction parameter. The region may be a first region and the phase-state model may be adjusted for a signal droop rate that is obtained by a method comprising: receiving signal data relating to nucleotide incorporation events in a plurality of wells within a second region of the array, wherein the plurality of wells includes the well containing the sample nucleic acid template, wherein the second region is the same or different from the first region; calculating a set of averaged signal values from the signal data; and determining a region-wide signal droop rate by fitting a signal decay function to the set of averaged signal values.

According to an embodiment, there is provided a non-transitory machine-readable storage medium comprising instructions which, when executed by a processor, cause the processor to perform the above method steps or similar steps. According to an embodiment, there is provided an apparatus comprising: a machine-readable memory; and a processor configured to execute machine-readable instructions, said instructions which when executed cause the apparatus to perform the above method steps or similar steps. The apparatus may further comprise: a plurality of reservoirs comprising different nucleotide reagents; and a flow chamber for receiving the nucleotide reagents.

According to an embodiment, there is provided a method of sequencing a sample nucleic acid template. In the method, signal data relating to nucleotide incorporation events resulting from a series of flows of nucleotides onto an array of wells are received. The array of wells may include (i) a first well containing the sample nucleic acid template and (ii) a plurality of other sample-containing wells. Then, preliminary sequence information for the sample nucleic acid template may be determined using signal data from the first well. Then, a phase-state model for a first set of nucleotide flows that contributed at least in part to the sequence information may be constructed based on signal data from the other sample-containing wells. The model may include a signal correction parameter fitted based on signal data from the other sample-containing wells. Fitting of the signal correction parameter may be done by comparing signal data from the plurality of other sample-containing wells to predicted signals for the plurality of other sample-containing wells resulting from the first set of nucleotide flows, which may be done using embodiments of a phase-state model as described in the present specification. The phase-state model may be stored in a machine-readable memory. Then, revised sequence information for the sample nucleic acid template may be determined by performing a base calling analysis of the signal data from the first well using the signal correction parameter fitted based on the other sample-containing wells. Base calling may be performed using any suitable base calling method, including for example as described in Sikora et al., U.S. patent application Ser. No. 13/588,408, filed Aug. 17, 2012, and in Sikora et al., U.S. patent application Ser. No. 13/645,058, filed Oct. 4, 2012, which are incorporated by reference herein in their entirety.

According to an embodiment, there is provided a method of sequencing a sample nucleic acid template, comprising: (a) receiving signal data relating to nucleotide incorporation events resulting from a series of flows of nucleotides onto an array of wells including (i) a first well containing the sample nucleic acid template and (ii) a plurality of other sample-containing wells; (b) determining preliminary sequence information for the sample nucleic acid template using the signal data from the first well; (c) constructing a phase-state model for a first set of nucleotide flows that contributed at least in part to the sequence information, wherein the model includes a signal correction parameter fitted by comparing signal data from the plurality of other sample-containing wells to predicted signals for the plurality of other sample-containing wells resulting from the first set of nucleotide flows, and wherein the model is stored in a machine-readable memory; and (d) determining revised sequence information for the sample nucleic acid template by performing a base calling analysis of the signal data from the first well using the signal correction parameter fitted based on signal data from the plurality of other sample-containing wells.

In various embodiments, the plurality of other sample-containing wells may be disposed in a region generally surrounding the first well. The plurality of other sample-containing wells may also be disposed in a region disparately located from the first well. The plurality of other sample-containing wells may also be disposed in a plurality of different regions. The signal correction parameter may be obtained using signal data obtained from at least a portion of the plurality of other sample-containing wells and without using signal data obtained from the first well. The signal correction parameter may be obtained using signal data obtained from at least a portion of the plurality of other sample-containing wells and signal data obtained from the first well. The method may further comprise performing steps (b) through (d) for each of the obtained signal data from each or some of the plurality of other sample-containing wells to obtain multiple fitted signal correction parameters, and each of the fitted signal correction parameters may be determined for a given well without using signal data from that given well. The method may further comprise calculating one or more region-wide estimates of the signal correction parameter using the multiple fitted signal correction parameters. The method may further comprise calculating a fitting metric that measures the fit between the predicted signals and the signal data. The fitting metric may measure the fit between the predicted signals and the signal data; and the region-wide estimate may exclude fitted signal correction parameters from wells that produce a fitting metric exceeding a predetermined threshold. The method may further comprise repeating steps (c) through (d) using the fitted signal correction parameter. The phase-state model may include two or more signal correction parameters, which may include a carry forward rate and an incomplete extension rate. The method may further comprise calculating a fitting metric that measures a fit between the predicted signals and the signal data. The method may further comprise determining a value of the signal correction parameter that optimizes the fitting metric. The method may further comprise determining a value of the signal correction parameter using Nelder-Mead optimization. The fitting metric may be calculated using only nucleotide flows that result in nucleotide non-incorporation or single nucleotide incorporations.

According to an embodiment, there is provided a non-transitory machine-readable storage medium comprising instructions which, when executed by a processor, cause the processor to perform the above method steps or similar steps. According to an embodiment, there is provided an apparatus comprising: a machine-readable memory; and a processor configured to execute machine-readable instructions, said instructions which when executed cause the apparatus to perform the above method steps or similar steps. The apparatus may further comprise: a plurality of reservoirs comprising different nucleotide reagents; and a flow chamber for receiving the nucleotide reagents.

According to an embodiment, there is provided a method of sequencing a sample nucleic acid template contained in a well of an array having multiple wells, comprising: receiving signal data relating to chemical reactions in a plurality of wells within a region of the array resulting from a flow of nucleotides to the array, wherein the plurality of wells includes the well containing the sample nucleic acid template; calculating a set of averaged signal values from the signal data, wherein the set of averaged signal values are stored in a machine-readable memory, and wherein the averaged signal values are determined based on signal data from one or more wells other than the well containing the sample nucleic acid template; determining a region-wide signal droop rate by fitting a signal decay function to the set of averaged signal values; and storing the region-wide signal droop rate in the memory.

According to an embodiment, there is provided a non-transitory machine-readable storage medium comprising instructions which, when executed by a processor, cause the processor to perform the above method steps or similar steps. According to an embodiment, there is provided an apparatus comprising: a machine-readable memory; and a processor configured to execute machine-readable instructions, said instructions which when executed cause the apparatus to perform the above method steps or similar steps. The apparatus may further comprise: a plurality of reservoirs comprising different nucleotide reagents; and a flow chamber for receiving the nucleotide reagents.

The present teachings may use any of various techniques for detecting the nucleotide incorporation(s). For example, some sequencing-by-synthesis techniques operate by the detection of pyrophosphate (PPi) released by the incorporation reaction (see e.g., U.S. Pat. Nos. 6,210,891; 6,258,568; and 6,828,100). In another example, some sequencing-by-synthesis techniques detect labels associated with the nucleotides, such as mass tags, fluorescent, and/or chemiluminescent labels. Where detectable labels are used, an inactivation step may be included in the workflow (e.g. by chemical cleavage or photobleaching) prior to the next cycle of synthesis and detection. The present teachings may be particular useful for sequencing methods that operate by single-nucleotide addition, in which the precursor nucleotides are repeatedly added individually to the reaction in series according to a predetermined ordering. Examples of such sequencing techniques include those based on the detection of inorganic pyrophosphate or hydrogen ions produced by the incorporation reactions.

The reactions may be carried out on microwell sensor arrays, such as those described in U.S. Patent Application Publication No. 2010/0300559, No. 2010/0197507, No. 2010/0301398, No. 2010/0300895, No. 2010/0137143, and No. 2009/0026082, and U.S. Pat. No. 7,575,865, which are incorporated by reference herein. The microwell sensor array has multiple wells for carrying out the sequencing reactions. In some cases, the sensor array is a chemFET sensor array. In some cases, the chemFET sensors of the sensor array detects hydrogen ions. In some cases, flowing of the reagent(s) onto the sensor array causes chemical reactions that release hydrogen ions. In some cases, the amplitude of the signals from the chemFET sensors is related to the amount of hydrogen ions detected. In some cases, the sensor array is a light-sensing array. In some cases, flowing of the reagent(s) onto the sensor array causes chemical reactions that release inorganic pyrophosphate, which causes the emission of light via an enzyme cascade initiated by the inorganic pyrophosphate.

In certain embodiments, the present teachings may use a pH-based method of detecting nucleotide incorporation(s). Such an approach may measure the amount of hydrogen ions released from the polymerase-catalyzed incorporation reactions. In pH-based methods for DNA sequencing, base incorporations can be determined by measuring the hydrogen ions that are generated. Additional details of pH-based sequence detection systems and methods can be found in commonly-assigned U.S. Patent Application Publication No. 2009/0127589 and No. 2009/0026082, which are incorporated by reference.

In pH-based detection methods, the production of hydrogen ions may be monotonically related to the number of contiguous complementary bases in the template strands (as well as the total number of template strands with primer and polymerase that participate in an extension reaction). Thus, when there is a number of contiguous identical complementary bases in the template (i.e. a homopolymer region), the number of hydrogen ions generated is generally proportional to the number of contiguous identical complementary bases. The corresponding output signals may sometimes be referred to as "1-mer", "2-mer", "3-mer" output signals, and so on, based on the expected number of repeating bases. Where the next base in the template is not complementary to the flowed nucleotide, generally no incorporation occurs and there is no substantial release of hydrogen ions (in which case, the output signal is sometimes referred to as a "0-mer" output signal).

Figure 6:
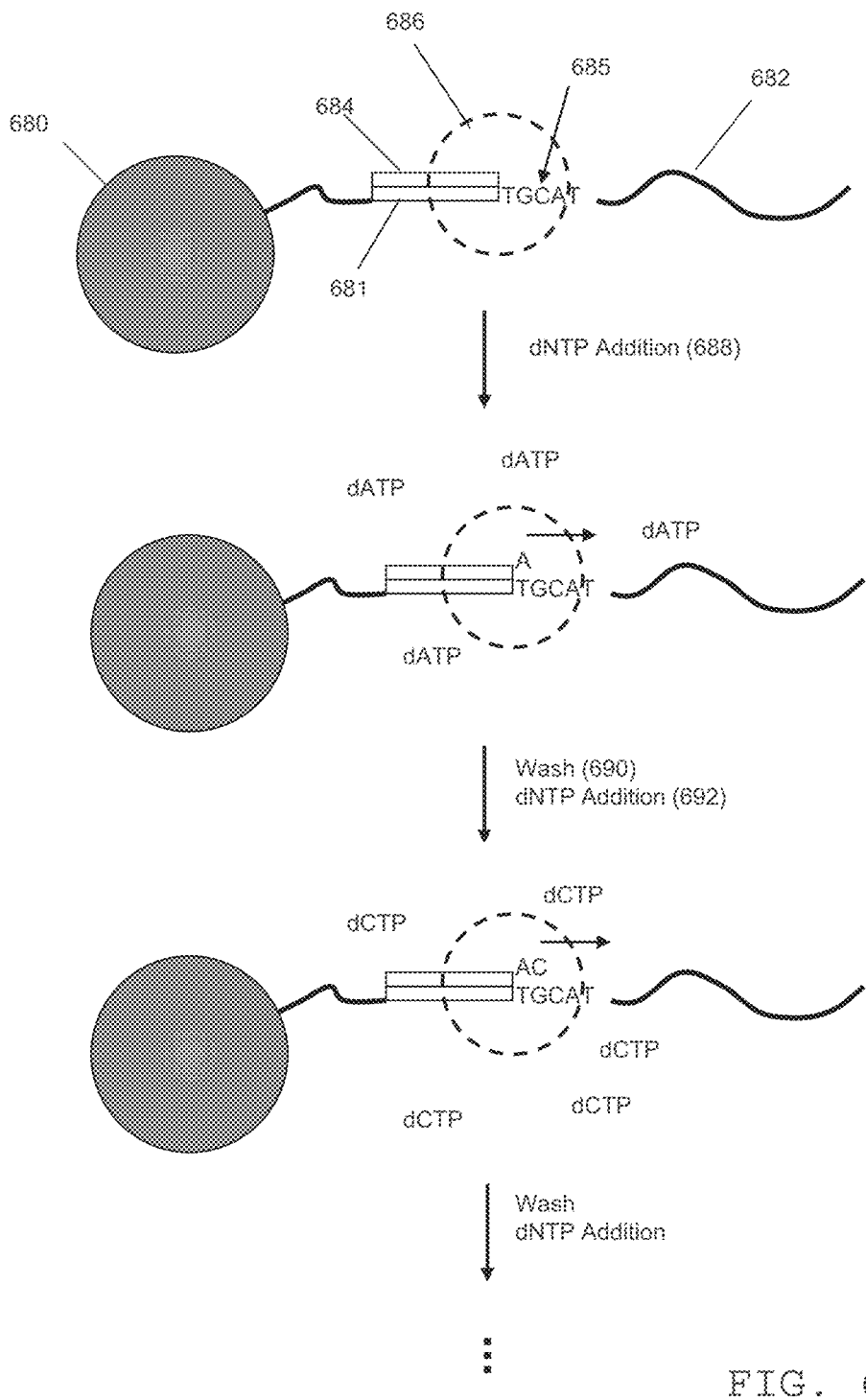
FIG. 6 shows an example of a sequencing-by-synthesis operation.

In each wash step of the cycle, a wash solution (typically having a predetermined pH) is used to remove residual nucleotide of the previous step in order to prevent misincorporations in later cycles. Usually, the four different kinds of nucleotides (e.g. dATP, dCTP, dGTP, and dTTP) are flowed sequentially to the reaction chambers, so that each reaction is exposed to one of the four different nucleotides for a given flow, with the exposure, incorporation, and detection steps being followed by a wash step. An example of this process is illustrated in FIG. 6, which shows a template polynucleotide strand 682 attached to a particle 680. Primer 684 is annealed to template strand 682 at its primer binding site 681. A DNA polymerase 686 is operably bound to the template-primer duplex. Template strand 682 has the sequence 685, which is awaiting complementary base incorporation. Upon the flow of the nucleotide (shown as dATP), polymerase 686 incorporates a nucleotide since "T" is the next nucleotide in template strand 682 (because the "T" base is complementary to the flowed dATP nucleotide). Wash step 690 follows, after which the next nucleotide (dCTP) is flowed 692. Optionally, after each step of flowing a nucleotide, the reaction chambers may be treated with a nucleotide-destroying agent (such as apyrase) to eliminate any residual nucleotides remaining in the chamber, which can cause spurious extensions in subsequent cycles.

Figure 7:
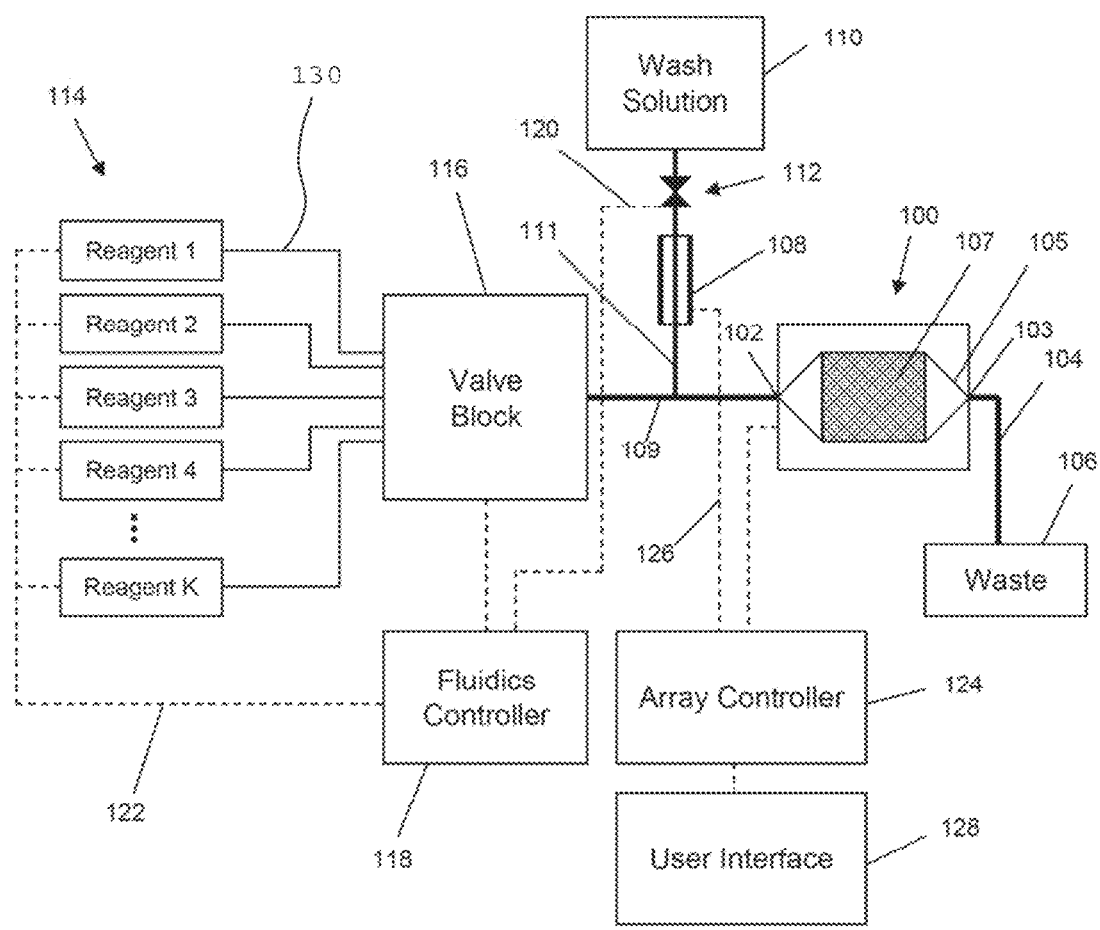
FIG. 7 is a diagram showing a sequencing apparatus according to an embodiment of the present invention.

The present teachings also provide an apparatus for sequencing polynucleotide strands according to the method of the present teachings. A particular example of an apparatus of the present teachings is shown in FIG. 7. The apparatus of FIG. 7 is configured for pH-based sequencing and includes multiple reservoirs for containing nucleotide reagents 1 through K (114). These reagents contain the nucleotides to be flowed for the sequencing process. The reagents 114 are flowed through fluid passages 130 and through a valve block 116 that controls the flow of the reagents to flow chamber 105 (also referred to herein as a reaction chamber) via fluid passage 109. The apparatus includes a reservoir 110 for containing a wash solution that is used to wash away the nucleotide reagent of the previous step. Reagents are discarded through waste passage 104 into a waste container 106 after exiting the flow chamber 105.

The apparatus also includes a fluidics controller 118, which may programmed to control the flow from the multiple reagent reservoirs to the flow chamber according to a predetermined ordering that comprises an alternate flow ordering, as described above. For this purpose, fluidics controller 118 may be programmed to cause the flow of reagents 114 from the reagents reservoir and operate the valves 112 and 116. The fluidics controller may use any conventional instrument control software, such as LabView (National Instruments, Austin, Tex.). The reagents may be driven through the fluid pathways 130, valves, and flow cell by any conventional mechanism such as pumps or gas pressure.

The apparatus also has a valve 112 for controlling the flow of wash solution into passage 109. When valve 112 is closed, the flow of wash solution is stopped, but there is still uninterrupted fluid and electrical communication between reference electrode 108, passage 109, and sensor array 100. Some of the reagent flowing through passage 109 may diffuse into passage 111, but the distance between reference electrode 108 and the junction between passages 109 and 111 is selected so that little or no amount of the reagents flowing in common passage 109 reach reference electrode 108. This configuration has the advantage of ensuring that reference electrode 108 is in contact with only a single fluid or reagent throughout an entire multi-step reaction process.

As shown in FIG. 7, flow chamber 105 is loaded with a flow cell that includes an inlet 102, an outlet 103, and a microwell array 107 which is operationally associated with a sensor array 100 that measures physical and/or chemical parameters in the microwells that provide information about the status of a reaction taking place therein; or in the case of empty wells, information about the physical and/or chemical environment in the flow cell. Each microwell may have a sensor for detecting an analyte or reaction property of interest. In this particular embodiment, the microwell array is integrated with the sensor array as a single chip. A flow cell can have a variety of designs for controlling the path and flow rate of reagents over the microwell array. This particular apparatus has an array controller 126 which receives information from sensor array 100 and reference electrode 108 via communication line 126. A user interface 128 provides an interface through which a user may interact with the apparatus.

Figure 8:
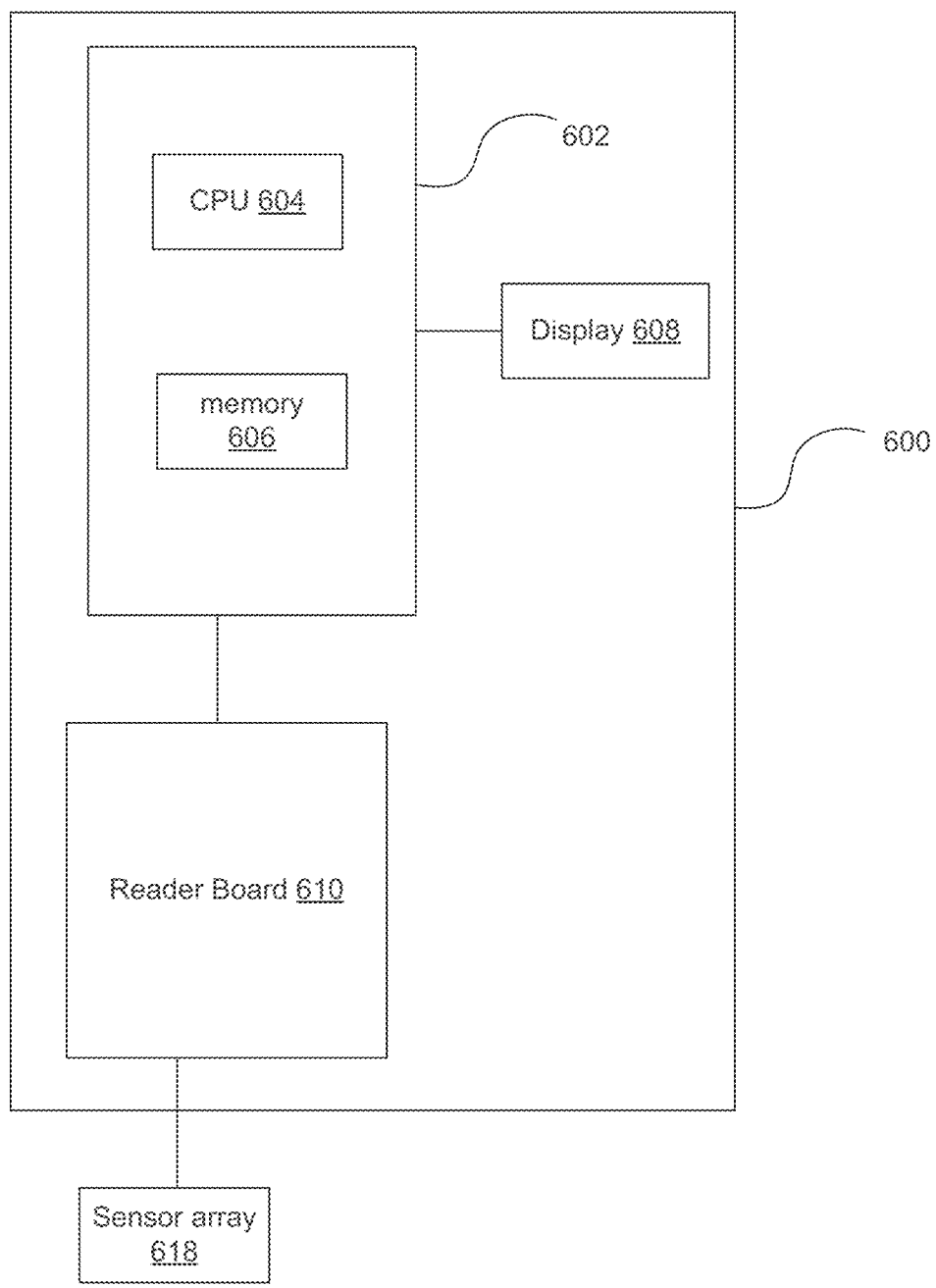
FIG. 8 shows an apparatus according to an embodiment of the present invention.

An apparatus may be used to perform the above-described methods of the present teachings. The apparatus may be a computer that includes various components such as processor(s) and memory. An example of an apparatus of the present teachings is shown in FIG. 8. In some embodiments, the apparatus 600 may include one or more processors 604 and machine-readable memory 606. In some embodiments, the apparatus may include a display 608. In some embodiments, the apparatus may include a reader board 610 which is coupled to a sensor array 618. The reader board 610 may include various components used in signal processing, including analog-to-digital converters. In some embodiments the apparatus may be part of the sequencing apparatus. In other embodiments, the apparatus may be separate from the sequencing apparatus; in some embodiments the apparatus may be coupled to the sequencing apparatus.

In various embodiments, a polynucleotide may be represented by a sequence of letters (upper or lower case), such as "ATGCCTG," and it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context.

Polynucleotides may comprise the four natural nucleosides (e.g. deoxyadenosine, deoxycytidine, deoxyguanosine, deoxythymidine for DNA or their ribose counterparts for RNA) linked by phosphodiester linkages. However, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity (e.g. single stranded DNA, RNA/DNA duplex, or the like), then selection of an appropriate composition for the oligonucleotide or polynucleotide substrates is well within the knowledge of one of ordinary skill, especially with guidance from treatises such as Sambrook et al, MOLECULAR CLONING, 2nd ed. (Cold Spring Harbor Laboratory, New York, 1989), and like references.

"Polynucleotide" refers to a linear polymer of nucleotide monomers and may be DNA or RNA. Monomers making up polynucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g., naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. As used herein, the term "oligonucleotide" refers to smaller polynucleotides, for example, having 5-40 monomeric units.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or rewriteable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, or the like, including any medium suitable for use in a computer. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

According to other embodiments of the present teachings, any one or more features of any one or more of the above-discussed teachings and/or exemplary embodiments may be performed or implemented at least partly using a cloud computing resource.

Those skilled in the art may appreciate from the foregoing description that the present teachings may be implemented in a variety of forms, and that the various embodiments may be implemented alone or in combination. Therefore, while the embodiments of the present teachings have been described in connection with particular examples thereof, the true scope of the embodiments and/or methods of the present teachings should not be so limited since other modifications will become apparent to the skilled practitioner upon a study of the drawings, specification, and following claims.

What is claimed is:

1. A method of sequencing a sample nucleic acid template, comprising:
(a) measuring signal data relating to nucleotide incorporation events resulting from a series of flows of nucleotides onto an array of wells including (i) a first well containing the sample nucleic acid template and (ii) a plurality of other sample-containing wells, wherein the array includes a sensor array for detecting the signal data related to the chemical reactions resulting from the flow of nucleotides, wherein the signal data are received from the sensor array;
(b) determining preliminary sequence information for the sample nucleic acid template using the signal data from the first well;
(c) constructing a phase-state model for a first set of nucleotide flows that contributed at least in part to the sequence information, wherein the model includes a signal correction parameter fitted by comparing signal data from the plurality of other sample-containing wells to predicted signals for the plurality of other sample-containing wells resulting from the first set of nucleotide flows, and wherein the model is stored in a machine-readable memory; and (d) determining revised sequence information for the sample nucleic acid template by performing a base calling analysis of the signal data from the first well using the signal correction parameter fitted based on signal data from the plurality of other sample-containing wells, wherein the first well containing the sample nucleic acid template is part of a first set of wells in a first region of the array, the plurality of other sample-containing wells are part of a second set of wells in the first region of the array, and the first set of wells and the second set of wells are distinguishable from one another within the first region of the array by shape, dimension, or inclusion in a defined spatial arrangement that is an alternating arrangement wherein positions of the wells of the first set of wells alternate with positions of the wells of the second set of wells, and wherein the array further includes additional regions of the array that have additional respective first and second sets of wells that are distinguishable from one another within each of the additional regions of the array.

2. The method of claim 1, wherein the first set of wells and the second set of wells in each of the first region of the array and the additional regions of the array are distinguishable from one another within each respective region of the array by inclusion in the defined spatial arrangement that is the alternating arrangement wherein the positions of the wells of the first set of wells alternate with the positions of wells of the second set of wells in each of the first region and the additional regions.

3. The method of claim 1, further comprising:
performing steps (c) and (d) for the signal data from each or some of the plurality of other sample-containing wells to obtain multiple signal correction parameters, wherein each of the multiple signal correction parameters is determined for a given well without using signal data from that given well.

4. The method of claim 1, wherein the phase-state model includes two or more signal correction parameters, including a carry forward rate and an incomplete extension rate.

5. The method of claim 1, further comprising:
calculating, using the phase-state model, the predicted signals for the plurality of other sample-containing wells resulting from the set of nucleotide flows;
comparing the predicted signals to the signal data from the plurality of other sample-containing wells;
fitting the signal correction parameter of the phase-state model based on the comparison of the predicted signals to the signal data from the plurality of other sample-containing wells.

6. The method of claim 5, wherein the comparing step comprises calculating a fitting metric that measures a fit between the predicted signals and the signal data.

7. The method of claim 6, wherein the fitting step comprises determining a value of the signal correction parameter that optimizes the fitting metric.

* * * * *